(12) United States Patent
Varadhachary et al.

(10) Patent No.: US 7,901,879 B2
(45) Date of Patent: Mar. 8, 2011

(54) LACTOFERRIN IN THE TREATMENT OF MALIGNANT NEOPLASMS AND OTHER HYPERPROLIFERATIVE DISEASES

(75) Inventors: Atul Varadhachary, Houston, TX (US);
Rick Barsky, Houston, TX (US);
Federica Pericle, Houston, TX (US);
Karel Petrak, Houston, TX (US);
Yenyun Wang, Houston, TX (US)

(73) Assignee: Agennix Incorporated, Houston, TX (US)

( * ) Notice: Subject to any disclaimer, the term of this patent is extended or adjusted under 35 U.S.C. 154(b) by 669 days.

(21) Appl. No.: 10/434,769

(22) Filed: May 9, 2003

(65) Prior Publication Data
US 2004/0009895 A1    Jan. 15, 2004

Related U.S. Application Data

(60) Provisional application No. 60/379,442, filed on May 10, 2002, provisional application No. 60/379,441, filed on May 10, 2002, provisional application No. 60/379,474, filed on May 10, 2002.

(51) Int. Cl.
*A61K 38/16* (2006.01)
*A61P 35/04* (2006.01)

(52) U.S. Cl. ................... 435/6; 514/6; 514/12

(58) Field of Classification Search ........... 435/6; 514/6
See application file for complete search history.

(56) References Cited

U.S. PATENT DOCUMENTS

| | | | |
|---|---|---|---|
| 4,977,137 A | 12/1990 | Nichols et al. | |
| 5,198,419 A | 3/1993 | Ando et al. | |
| 5,571,691 A | 11/1996 | Conneely et al. | |
| 5,571,697 A | 11/1996 | Conneely et al. | |
| 5,571,896 A | 11/1996 | Conneely et al. | |
| 5,766,939 A | 6/1998 | Conneely et al. | |
| 5,849,881 A | 12/1998 | Conneely et al. | |
| 5,955,316 A | 9/1999 | Conneely et al. | |
| 6,080,559 A | 6/2000 | Conneely et al. | |
| 6,100,054 A | 8/2000 | Conneely et al. | |
| 6,111,081 A | 8/2000 | Conneely et al. | |
| 6,228,614 B1 * | 5/2001 | Conneely et al. ........... | 435/69.1 |
| 6,333,311 B1 | 12/2001 | Nuijens et al. | |
| 6,399,570 B1 | 6/2002 | Mann | |
| 6,635,447 B1 | 10/2003 | Conneely et al. | |
| 6,890,902 B2 | 5/2005 | Svendsen et al. | |
| 2003/0022821 A1 * | 1/2003 | Svenden et al. ................. | 514/12 |
| 2003/0096736 A1 | 5/2003 | Kruzel et al. | |
| 2003/0105006 A1 | 6/2003 | Mann | |
| 2003/0190303 A1 | 10/2003 | Kimber et al. | |
| 2004/0009896 A1 | 1/2004 | Glynn et al. | |
| 2004/0082504 A1 * | 4/2004 | Varadhachary et al. ......... | 514/6 |
| 2004/0142037 A1 | 7/2004 | Engelmayer et al. | |
| 2005/0064546 A1 | 3/2005 | Conneely et al. | |
| 2005/0075277 A1 | 4/2005 | Varadhachary et al. | |
| 2010/0137208 A1 * | 6/2010 | Varadhachary et al. ........ | 514/12 |

FOREIGN PATENT DOCUMENTS

| | | |
|---|---|---|
| EP | 0730868 A1 | 9/1996 |
| JP | 63051337 | 3/1988 |
| JP | 05186368 | 7/1993 |
| JP | 2001-504447 | 2/1999 |
| JP | 2002-519332 | 6/1999 |
| JP | 2000229881 | 8/2000 |
| WO | WO-9806425 A1 | 2/1998 |
| WO | 9833509 A2 | 8/1998 |
| WO | WO-9844940 A1 | 10/1998 |
| WO | WO-0203910 A2 | 1/2002 |
| WO | WO-2006/054908 | 5/2006 |

OTHER PUBLICATIONS

McColl GJ. Med. J. Aust. 175: S108-S111, 2001; referenced as printout pp. 1-8.*
Gordon KB et al. J. Am. Acad. Dermatol. 54(3): S85-S91, 2006.*
Smorenburg et al. European Journal of Cancer 37: 2310-2323, 2001.*
Kuhara T et al. Nutrition and Cancer 38(2): 192-199, 2000.*
Ogura T et al. Blood 98(7): 2101-2107, 2001.*
Inaba K et al. Proc. Natl. Acad. Sci. USA 90: 3038-3042, 1993.*
Walter KA et al. Neurosurgery 37(6): 1129-1145, 1995.*
Gustalla et al. British Journal of Cancer89: S16-S22, 2003.*
Lebwohl et al. European Journal of Cancer 34(10): 1522-1534, 1998.*
Griffiths CEM et al. British Journal of Dermatology 144: 715-725, 2001.*
Krzakowski M. Lung Cancer 34: S159-S163, 2001.*
Voskoglou-Nomikos et al. (Clin. Can. Res. 9:4227-4239 (2003)).*
Definition of "Alimta".*
Talmadge et al. (Am. J. Pathol 170(3):793-804 (2007)).*
Ushida et al (Japn. J. Cancer Res. 90: 262-267 (Mar. 1999).*
Loughlin et al. (Can. 59(3):566-571 (1987); Abstract).*
U.S. Appl. No. 10/733,621, Agennix Incorporated.
U.S. Appl. No. 10/732,429, Agennix Incorporated.
U.S. Appl. No. 10/844,865, Agennix Incorporated.
U.S. Appl. No. 10/728,521, Agennix Incorporated.
U.S. Appl. No. 10/862,213, Agennix Incorporated.
U.S. Appl. No. 10/728,275, Agennix Incorporated.
Amouric et al, "Effect of Lactoferrin on the Growth of a Human Colon Adenocarcinoma Cell Line—Comparison with Transferrin," in Vitro vol. 20 No. 7, Jul. 1984, pp. 543-548.
Barresi et al, "Lactoferrin in Benign Hypertrophy and Carcinomas of the Prostatic Gland," Virchows Archiv (Pathol Anat) 403; 1984, pp. 59-66.
Shau et al, "Modulation of Natural Killer and Lymphokine-activated Killer Cell Cytotoxicity by Lactoferrin," Journal of Leukocyte Biology vol. 51, Apr. 1992, pp. 343-349.
Brock et al, "Interaction of LActoferrin with Mononuclear and Colon Carcinoma cells," Lactoferrin—Structure and Function, T.W. Hutches, S.V. Rumball and B. Lonnerdal. New York, Plenum PRess: pp. 157-169.
Bezault et al, "Human Lactoferrin Inhibits Growth of Solid Tumors and Development of Experimental Metastases in Mice," Cancer Research 54, May 1, 1994, pp. 2310-2312.

(Continued)

*Primary Examiner* — Lynn Bristol
(74) *Attorney, Agent, or Firm* — Fulbright & Jaworski L.L.P.

(57) ABSTRACT

The present invention relates to methods of treating a hyperproliferative disease by administering a composition of lactoferrin alone or in combination with standard anti-cancer therapies.

2 Claims, 5 Drawing Sheets

OTHER PUBLICATIONS

Sekine et al, "Inhibition of Azoxymethane-initiated Colon Tumor by Bovine Lactoferrin Administration in F344 Rats," Jpn. J. Cancer Res. 88, Jun. 1997, pp. 523-526.

Yoo et al, "Bovine Lactoferrin and Lactoferricin, a Peptide Derived from Bovine Lactoferrin, Inhibit Tumor Metastasis in mice," Jpn. J. Cancer Res. 88, Feb. 1997, pp. 184-190.

Tsuda et al, Inhibition of Azoxymethane Initiated Colon Tumor and Aberrant Crypt FOCI Development by Bovine Lactoferrin Administration in F344 Rats, Advances in Lactoferrin research, edited by Spik et al, Plenum Press, New York, 1998, pp. 273-283.

Damiens et al, "Effects of Human Lactoferrin on NK Cell Cytotoxicity Against Haematopoietic and Epithelial Tumour Cells," Biochimica et Biophysica Acta 1402, 1998, pp. 277-287.

Ushida et al, "Inhibitory Effects of Bovine Lactoferrin on Intestinal Polyposis in the Apc Mouse," Cancer Letters 134, 1998, pp. 141-145.

Yoo et al, "Bovine Lactoferrin and Lactoferricin Inhibit Tumor Metastasis in Mice," Advances in Lactoferrin Research, Chapter 35, Plenum Press, New York, 1998, pp. 285-291.

Sakamoto, N., "Antitumor Effect of Human Lactoferrin against Newly Establishes Human Pancreatic Cancer Cell Line SPA," Gan to Kagaku Ryoho, Aug. 1998 25(10), pp. 1557-1563.

Ushida et al, "Possible Chemopreventive Effects of Bovine Lactoferrin on Esophagus and Lung Carcinogenesis in the Rat," Jpn. J. Cancer Res. 90, Mar. 1999, pp. 262-267.

Damiens et al, "Lactoferrin Inhibits G1 Cyclin-Dependent Kinases During Growth Arrest of Human Breast Carcinoma Cells," Journal of Cellular Biochemistry 72, 1999, pp. 486-498.

Iigo et al, "Inhibitory Effects of Bovine Lactoferrin on Colon Carcinoma 26 Lung Metastasis in Mice," Clinical & experimental Metastasis 17, 1999, pp. 35-40.

Masuda et al, "Chemopreventive Effects of Bovine Lactoferrin on N-Butyl-N (4-hydroxybutyl) Nitrosamine-Induced Rat Bladder Carcinogenesis," Jpn. J. Cancer Res. 91, Jun. 2000, pp. 582-588.

Tanaka et al, "Bovine Lactoferrin Inhibits Rat Tongue Carcinogenesis," Elsevier Sciences B.V. Lactoferrin: Structure, Function and Applications 2000, pp. 401-411.

Tsuda et al, "Milk and Dairy Products in Cancer Prevention: Focus on Bovine Lactoferrin," Elsevier Science B.V.—Mutation Research 462, 2000, pp. 227-233.

Teng et al, "Lactoferrin Gene: Methylation, Expression and Cancer," Elseiver Science B.V.—Lactoferrin: Structure, Function and Application, 2000, pp. 247-255.

Kuhara et al, "Orally Administered Lactoferrin Exerts an Antimetastatic Effect and Enhances Production of IL-18 in the Intestinal Epithelium," Nutrition and Cancer, vol. 28 No. 2, 2000, pp. 192-199.

Tsuda et al, "Prevention of Carcinogenesis and Metastasis by Dietary Bovine Lactoferrin," Elsevier Sciences B.V.—Lactoferrin: Structure, Function and Applications, 2000, pp. 389-399.

Tsuda et al, "Prevention of Colon Carcinogenesis and Carcinoma Metastasis by Orally Administered Bovine Lactoferrin in animals," BioFactors 12, 2000, pp. 83-88.

Wang et al, "Activation of Intestinal Mucosal Immunity in Tumor-bearing Mice by Lactoferrin," Jpn. J. Cancer Res. 91, Oct. 2000, pp. 1022-1027.

Norby et al, "Orally Administered Bovine Lactoferrin Systemically Inhibits VEGF 165—Mediated Angiogenesis in the Rat," Int. j. Cancer 91, 2001, pp. 236-240.

Varadhachary et al., "Intratumoral Injection of human Recombinant Lactoferrin Inhibits the Growth of Human Tumors Implanted in Athymic Nude Mice," www.asco.org, Abstract No. 1875, 2002.

Varadhachary et al, "Recombinant Human Lactoferrin, a novel oral Anti-Cancer Drug," www.asco.org, Abstract No. 934, 2003.

van Belzen, nico, "The Role of Lactoferrin in Cancer Prevention," Sciences Des Aliments, 22, 2002, pp. 461-468.

Tsuda et al, "Cancer Prevention by Bovine Lactoferrin and Underlying Mechanisms—a Review of Experimental and Clinical Studies," Biochem. Cell Biol. 80, 2002, pp. 131-136.

Fujita et al, "Down-Regulation of 2-Amino-3, 8-dimethylimidazo [4,5-f] Quinoxaline (MeIQx)-induced CYP1A2 Expression is Associated with Bovine Lactoferrin Inhibition of MeIQx-induced Liver and Colon Carcinogenesis in Rats," Jpn. J. Cancer Res. 93, Jun. 2002, pp. 616-625.

Curcio C, Di Carlo E, Clynes R, Smyth MJ, Boggio K, Quaglino E, Spadaro M, Colombo MP, Amici A, Lollini PL, Musiani P, Forni G. Nonredundant roles of antibody, cytokines, and perforin in the eradication of established Her-2/neu carcinomas. J Clin Invest. Apr. 2003;111(8):1161-70.

Escudier B, Szczylik C, Eisen T, et al. Randomized Phase III trial of the Raf kinase and VEGFR inhibitor sorafenib (BAY 43-9006) in patients with advanced renal cell carcinoma (RCC). Proceedings from the 2005 annual meeting of the American Society of Clinical Oncology (ASCO). Abstract #LBA4510.

Hayes TG, Falchook GF, Varadhachary GR, Smith DP, Davis LD, Dhingra HM, Hayes BP, and Varadhachary A. Phase I trial of oral talactoferrin alfa in refractory solid tumors. Investigational New Drugs, 2006;24(3):233-40.

Mojaverian P, Robbins-Weilert D, Gbenado S, Burmaster S, Dimmitt D, Erasmus G, Abdou N, Varadhachary A, Yankee E, and Wang Y. Single and Multiple Dose Safety, Tolerability and Pharmacokinetics (PK) of Oral Recombinant Lactoferrin (rhLF) in Healthy Subjects. Proceedings of the annual meeting of the American Association of Pharmaceutical Scientists, 2003.

Ritchie DS, Hermans IF, Lumsden JM, Scanga CB, Roberts JM, Yang J (2000) Dendritic cell elimination as an assay of cytotoxic T lymphocyte activity in vivo. J Immunol Methods 246: 109-17.

Srinivas S., W. M. Stadler, R. Bukowski, R. Figlin, T. Hayes, E. W. Yankee, E. Jonasch, Talactoferrin alfa may prolong progression-free survival in advanced renal carcinoma patients. Journal of Clinical Oncology, 2006 ASCO Annual Meeting Proceedings Part I. vol. 24, No. 18S (Jun. 20 Supplement), 2006: 4600.

Varadhachary A, Wolf JS, Petrak K, O'Malley, JR. BW, Spadaro M, Curcio C, Forni G and Pericle F. Oral lactoferrin inhibits growth of established tumors and potentiates conventional chemotherapy. Int. J. Cancer, 111 : 398-403., 2004.

Wang Y, Yankee E, Varadhachary A, RhLF NSCLC Clinical Investigator Group. Double blind, Placebo Controlled Trial of Oral Lactoferrin in Combination Therapy for First Line Non-small Cell Lung Cancer (NSCLC). Journal of Clinical Oncology, 2005 ASCO Annual Meeting Proceedings. vol. 23, No. 16S, Part I of II (Jun. 1 Supplement), 2005: 7141.

Wang Y, Raghunadharao D, Raman G, Doval DC, Advani SH, Julka PK, Parikh PM, Patil S, Nag S, Madhavn J, Varadhachary A. Adding oral talactoferrin to first-line NSCLC chemotherapy safely enhanced efficacy in a randomized trial. Abstract #7095, Proceedings of the American Society of Clinical Oncology, 2006.

Yang JC, Haworth L, Sherry RM, et al. A randomized trial of bevacizumab, an anti-vascular endothelial growth factor antibody, for metastatic Renal Cancer. N Engl J Med. Jul. 31, 2003;349(5):427-34.

Beyer M, Schultze JL. "Regulatory T cells in cancer." Blood. Aug. 1, 2006;108(3):804-11.

Bruserud O, Wendelboe O. Biological treatment in acute myelogenous leukaemia: how should T-cell targeting immunotherapy be combined with intensive chemotherapy? Expert Opin Biol Ther. Nov. 2001;1(6):1005-16.

Cameron, M.D. et al. Temporal progression of metastasis in lung: cell survival, dormancy, and location dependence of metastatic inefficiency. Cancer Res. May 1, 2000;60(9):2541-6.

Costanzi JJ, Fletcher WS, Balcerzak SP, Taylor S, Eyre HJ, O'Bryan RM, Al-Sarraf M, Frank J. Combination chemotherapy plus levemisole in the treatment of disseminated malignant melanoma. A Southwest Oncology Group study. Cancer. Feb. 15, 1984;53(4):833-6.

De Gast GC, Vyth-Dreese FA, Nooijen W, Van Den Bogaard CJ, Sein J, Holtkamp MM, Linthorst GA, Baars JW, Schornagel JH, Rodenhuis S. Reinfusion of autologous lymphocytes with granulocyte-macrophage colony-stimulating factor induces rapid recovery of CD4+ and CD8+ T cells after high-dose chemotherapy for metastatic breast cancer. J Clin Oncol. Jan. 1, 2002;20(1):58-64.

Herberman RB. "Cancer immunotherapy with natural killer cells." Semin Oncol. Jun. 2002;29(3 Suppl 7):27-30.

Kageshita T, Hirai S, Ono T, Hicklin DJ, Ferrone S., "Down-regulation of HLA class I antigen-processing molecules in malignant melanoma: association with disease progression." Am J Pathol. Mar. 1999;154(3):745-54.

Kim R, Emi M, Tanabe K, Arihiro K., "Tumor-driven evolution of immunosuppressive networks during malignant progression." Cancer Res. Jun. 1, 2006;66(11):5527-36.

Lissoni P, Meregalli S, Fossati V, Paolorossi F, Barni S, Tancini G, Frigerio F. A randomized study of immunotherapy with low-dose subcutaneous interleukin-2 plus melatonin vs chemotherapy with cisplatin and etoposide as first-line therapy for advanced non-small cell lung cancer. Tumori. Dec. 31, 1994;80(6):464-7.

Mok TS, Leung TW. Changes in chemotherapy for pancreatic cancer. Hong Kong Med J. Dec. 1999;5(4):367-374.

Nowak AK, Robinson BW, Lake RA. Gemcitabine exerts a selective effect on the humoral immune response: implications for combination chemo-immunotherapy. Cancer Res. Apr. 15, 2002;62(8):2353-8.

Ohnuma T. Combination of chemotherapy and immunotherapy in man—review. Gan to Kagaku Ryoho. Aug. 1990;17(8 Pt 1)1428-36.

Osaki, T. et al., IFN—Inducing Factor/IL-18 Administration Mediates IFN—and IL-12-Independent Antitumor Effects, The Journal of Immunology, 1998, 160: 1742-1749.

Osterborg A, Henriksson L, Mellstedt H. Idiotype immunity (natural and vaccine-induced) in early stage multiple myeloma. Acta Oncol. 2000;39(7):797-800.

Robinson E, Haim N, Segal R, Veseley Z, Mekori T. Combined-modality treatment of inoperable lung cancer (i.v. immunotherapy, chemotherapy, and radiotherapy). Cancer Treat Rep. Mar. 1985;69(3):251-8.

Sekine K, Ushida Y, Kuhara T, Iigo M, Baba-Toriyama H, Moore MA, Murakoshi M, Satomi Y, Nishino H, Kakizoe T, Tsuda H. Inhibition of initiation and early stage development of aberrant crypt foci and enhanced natural killer activity in male rats administered bovine Lactoferrin concomitantly with azoxymethane. Cancer Lett. Dec. 23, 1997;121(2):211-6.

Uherek C, Tonn T, Uherek B, Becker S, Schnierle B, Klingemann HG, Wels W. Retargeting of natural killer-cell cytolytic activity to ErbB2-expressing cancer cells results in efficient and selective tumor cell destruction. Blood. Aug. 15, 2002;100(4):1265-73.

Van Den Broeke, L.T. et al. Dendritic cell-induced activation of adaptive and innate antitumor immunity. J Immunol. Dec. 1, 2003;171(11):5842-52.

Nowak AK, Lake RA, Robinson BW. Combined chemoimmunotherapy of solid tumours: Improving vaccines? Adv Drug Deliv Rev. Aug. 15, 2006; [Epub ahead of print].

Siefker-Radtke AO, Millikan RE, Tu SM, Moore DF Jr, Smith TL, Williams D, Logothetis CJ. Phase III trial of fluorouracil, interferon alpha-2b, and cisplatin versus methotrexate, vinblastine, doxorubicin, and cisplatin in metastatic or unresectable urothelial cancer. J Clin Oncol. Mar. 1, 2002;20(5)1361-7.

Atkins MB. Cytokine-based therapy and biochemotherapy for advanced melanoma. Clin Cancer Res. Apr. 1, 2006;12(7 Pt 2):2353s-2358s. Review.

Bajetta E, Del Vecchio M, Nova P, Fusi A, Daponte A, Sertoli MR, Queirolo P, Taveggia P, Bernengo MG, Legha SS, Formisano B, Cascinelli N. Multicenter phase III randomized trial of polychemotherapy (CVD regimen) versus the same chemotherapy (CT) plus subcutaneous interleukin-2 and interferon-alpha2b in metastatic melanoma. Ann Oncol. Apr. 2006;17(4):571-7. Epub Feb. 9, 2006.

Ridolfi R, Chiarion-Sileni V, Guida M, Romanini A, Labianca R, Freschi A, Lo Re G, Nortilli R, Brugnara S, Vitali P, Nanni O; Italian Melanoma Intergroup. Cisplatin, dacarbazine with or without subcutaneous interleukin-2, and interferon alpha-2b in advanced melanoma outpatients: results from an Italian multicenter phase III randomized clinical trial. J Clin Oncol. Mar. 15, 2002;20(6):1600-7.

Sommer AL, Wachel BK, Smith JA. Evaluation of vaccine dosing in patients with solid tumors receiving myelosuppressive chemotherapy. J Oncol Pharm Pract. Sep. 2006;12(3):143-54. Leuk Lymphoma. Aug. 2006;47(8):1570-82.

Schutt P, Brandhorst D, Stellberg W, Poser M, Ebeling P, Muller S, Buttkereit U, Opalka B, Lindemann M, Grosse-Wilde H, Seeber S, Moritz T, Nowrousian MR. Immune parameters in multiple myeloma patients: influence of treatment and correlation with opportunistic infections. Leuk Lymphoma. Aug. 2006;47(8):1570-82.

Becerra CR, Frenkel EP, Ashfaq R, Gaynor RB, Increased toxicity and lack of efficacy of Rofecoxib in combination with chemotherapy for treatment of metastatic colorectal cancer: A phase II study, Int. J. Cancer: 105, 868-872 [2003].

Lens MB, Reiman T, Husain AF. Abstract Use of tamoxifen in the treatment of malignant melanoma. Cancer. Oct. 1, 2003;98(7):1355-61. Review.

Nowak A, Findlay M, Culjak G, Stockler M. Tamoxifen for hepatocellular carcinoma. Cochrane Database Syst Rev. 2004;(3):CD001024. Review.

Nowak AK, Stockler MR, Chow PK, Findlay M. Use of tamoxifen in advanced-stage hepatocellular carcinoma. A systematic review. Cancer. Apr. 1, 2005;103(7):1408-14.

Kramer R, Brown P. Should tamoxifen be used in breast cancer prevention? Drug Saf. 2004;27(13):979-89.

Early Breast Cancer Trialists' Collaborative Group. Effects of chemotherapy and hormonal therapy for early breast cancer on recurrence and 15-year survival: an overview of the randomised trials. Lancet. May 14-20, 2005;365(9472)1687-1717.

Szarka CE, Grana G, Engstrom PF, Chemoprevention of cancer, Curr Probl Cancer, Jan.-Feb. 1994;18(1):6-79.

Kelloff GJ, Lippman SM, Dannenberg AJ, Sigman CC, Pearce HL, Reid BJ, Szabo E, Jordan VC, Spitz MR, Mills GB, Papadimitrakopoulou VA, Lotan R, Aggarwal BB, Bresalier RS, Kim J, Arun B, Lu KH, Thomas ME, Rhodes HE, Brewer MA, Follen M, Shin DM, Parnes HL, Siegfried JM, Evans AA, Blot WJ, Chow WH, Blount PL, Maley CC, Wang KK, Lam S, Lee JJ, Dubinett SM, Engstrom PF, Meyskens FL Jr, O'Shaughnessy J, Hawk ET, Levin B, Nelson WG, Hong WK; AACR Task Force on Cancer Prevention., Progress in chemoprevention drug development: the promise of molecular biomarkers for prevention of intraepithelial neoplasia and cancer—a plan to move forward, Clin Cancer Res., Jun. 15, 2006; 12(12):3661-97.

Brinkman M, Buntinx F, Muls E, Zeegers MP. Use of selenium in chemoprevention of bladder cancer. Lancet Oncol. Sep. 2006;7(9):766-74. Review.

Unger JM, Thompson IM Jr, Leblanc M, Crowley JJ, Goodman PJ, Ford LG, Coltman CA Jr. Estimated impact of the Prostate Cancer Prevention Trial on population mortality. Cancer. Apr. 1, 2005; 103(7):1375-80.

Smith W, Saba N. Retinoids as chemoprevention for head and neck cancer: where do we go from here? Crit Rev Oncol Hematol. Aug. 2005:55(2):143-52.

Jaiyesimi IA, Buzdar AU, Decker DA, Hortobagyi GN, Use of tamoxifen for breast cancer: twenty-eight years later, J Clin Oncol., Feb. 1995;13(2):513-29.

Gelber RD, Cole BF, Goldhirsch A, Rose C, Fisher B, Osborne CK, Boccardo F, Gray R, Gordon NH, Bengtsson NO, Sevelda P, Adjuvant chemotherapy plus tamoxifen compared with tamoxifen alone for postmenopausal breast cancer: meta-analysis of quality-adjusted survival, Lancet., Apr. 20, 1996;347(9008):1066-71).

Steinbach G, Lynch PM, Phillips RK, Wallace MH, Hawk E, Gordon GB, Wakabayashi N, Saunders B, Shen Y, Fujimura T, Su LK, Levin B, The effect of celecoxib, a cyclooxygenase-2 inhibitor, in familial adenomatous polyposis, N Engl J Med. Jun. 29, 2000; 342(26):1946-52.

Thompson IM, Goodman PJ, Tangen CM, Lucia MS, Miller GJ, Ford LG, Lieber MM, Cespedes RD, Atkins JN, Lippman SM, Carlin SM, Ryan A, Szczepanek CM, Crowley JJ, Coltman CA Jr The influence of finasteride on the development of prostate cancer. N Engl J Med. Jul. 17, 2003;349(3):215-24. Epub Jun. 24, 2003.

Motzer RJ, Bacik J, Schwartz LH, Reuter V, Russo P, Marion S, Mazumdar M. Prognostic Factors for Survival in Previously Treated Patients with Metastatic Renal Cell Carcinoma. J of Clin Oncology. Feb. 3, 2004; 22(3):454-63.

Varadhachary A, Spadaro M, Curcio C, Valli TVE, Mokyr MB, Blezinger P, Petrak K, Cavallo F, Pericle F, and Forni G. Oral Talactoferrin Alfa a Novel Anti-Cancer Therapy: Experimental and Clinical Experience. Invited Presentation, Second Cancer Vaccine Meeting, Siena, Dec. 2006.

Oldham, Robert K., "Development Therapeutics and the Design of Clinical Trials," p. 45-58 in Principles of Cancer Biotherapy, 4th edition (2003), ed. Robert K. Oldham, ISBN 140200706X.

Rosenberg, SA, Lotze MT, Yang JC, Aebersold PM, Linehan WM, Seipp CA and White DE. Experience with the use of high-dose interleukin-2 in the treatment of 652 cancer patients. *Ann Surg*. Oct. 1989;210(4):474-84.

Rovero S, Amici A, Carlo ED, Bei R, Nanni P, Quaglino E, Porcedda P, Boggio K, Smorlesi A, Lollini PL, Landuzzi L, Colombo MP, Giovarelli M, Musiani P, Forni G. DNA vaccination against rat her-2/Neu p185 more effectively inhibits carcinogenesis than transplantable carcinomas in transgenic BALB/c mice. J Immunol. Nov. 1, 2000;165(9):5133-42.

Smith LP, Thomas GR. Animal models for the study of squamous cell carcinoma of the upper aerodigestive tract: a historical perspective with review of their utility and limitations part B. Transgenic mouse models. Int J Cancer. May 15, 2006;118(10):2379-80. Review.

Teicher BA, Chen V, Shih C, Menon K, Forler PA, Phares VG, Amsrud T. Treatment regimens including the multitargeted antifolate LY231514 in human tumor xenografts. Clin Cancer Res. Mar. 2000;6(3):1016-23.

Dela Cruz JS, Lau SY, Ramirez EM, De Giovanni C, Forni G, Morrison SL, Penichet ML. Protein vaccination with the HER2/neu extracellular domain plus anti-HER2/neu antibody-cytokine fusion proteins induces a protective anti-HER2/neu immune response in mice. Vaccine. Mar. 28, 2003;21 (13-14):1317-26.

Fields MT, Eisbruch A, Normolle D, Orfali A, Davis MA, Pu AT, Lawrence TS. Radiosensitization produced in vivo by once- vs. twice-weekly 2'2'-difluoro-2'-deoxycytidine (gemcitabine). Int J Radiat Oncol Biol Phys. Jun. 1, 2000;47(3):785-91.

Grande C, Firvida JL, Navas V, Casal J. Interleukin-2 for the treatment of solid tumors other than melanoma and renal cell carcinoma. *Anticancer Drugs*, Jan. 2006;17(1):1-12.

Hung M. C., and Y. K. Lau. Basic science of Her-2/neu: a review. Semin. Oncol. 1999 26:51.

Noda, I, Fujieda S, Seki M, Tanaka N, Sunaga H, Ohtsubo T, Tsuzuki H, Fan GK, Saito H. Inhibition of N-linked glycosylation by tunicamycin enhances sensitivity to cisplatin in human head-and-neck carcinoma cells. Int J Cancer. Jan. 18, 1999;80(2):279-84.

IND 11728-023 Annual Report—Cover Letter.

FDA correspondence regarding IND 11728.

Food and Drug Administration, Office of Orphan Drug Products Development, letter of approval of orphan drug designation request #03-1822, Sep. 29, 2006.

AGENNIX submission to the Food and Drug Administration, Office Of Orphan Drug Products Development, in support of orphan drug designation request #03-1822 filed Jul. 11, 2006.

AGENNIX submission to the Food and Drug Administration, Office Of Orphan Drug Products Development, in support of orphan drug designation request #03-1822 filed Sep. 8, 2006.

Food and Drug Administration, Office Of Orphan Drug Products Development, letter of approval of orphan drug designation request #07-2367, Aug. 8, 2007.

AGENNIX submission to the Food and Drug Administration, Office Of Orphan Drug Products Development, in support of orphan drug designation request #07-2367 filed Dec. 29, 2006.

AGENNIX submission to the Food and Drug Administration, Office Of Orphan Drug Products Development, in support of orphan drug designation request #07-2367 filed May 18, 2007.

Cumulative list of Designated and or Approved Orphan Products Effective: May 16, 2008 http://www.fda.gov/orphan/designat/list.xls.

NCI Issues Clinical Announcement for Preferred Method of Treatment for Advanced Ovarian Cancer: Questions and Answers http://www.cancer.gov/newscenter/pressreleases/IPchemotherapyQandA.

Questions and Answers about Eloxatin (oxaliplatin for injection) http://www.fda.gov/cder/drug/infopage/eloxatin/default.htm.

Kerbel, RS, (2003) Human Tumor Xenografts as Predictive Preclinical Models for Anticancer Drug Activity in Humans, Cancer Biology & Therapy 2:4:Suppl. S134-S139.

Radiation Therapy for Cancer: Questions and Answers http://www.cancer.gov/cancertopics/factsheet/Therapy/radiation.

Iigo et al, "Fluctuation of Cytokine In Mucosa Of Small Intestine and T-Cell By Lactoferrin," Summaries Of The Annual Meeting Of The Pharmaceutical Society of Japan. Mar. 5, 2001. vol. 121(3):29.

Kuhara, "Induced IL- 18 Production From Intestinal Epithelium By Lactoferrin And Significance Thereof," Clinical Immunology, Sep. 25, 2000. vol. 34(3): 376-381.

Sakamoto, "Establishment of Human Pancreas Cancer Cell Line (SPA), Iron-Binding Glycoproteins, Antiproliferative Activity Of Human Lactoferrin," Cancer and Chemotherapy, Aug. 1998. vol. 258 (10): 1557-1563.

Hayes et al., "Phase I/II Trial Of Oral Talactoferrin In The Treatment Of Metastatic Solid Tumors," Investigational New Drugs, Feb. 24, 2009. 7 pages.

Jonasch et al, "Phase II Trial of Talactoferrin In Previously Treated Patients With Metastatic Renal Cell Carcinoma," Cancer, 2008,113(1):72-7.

Lee et al., "Protein Drug Oral Delivery: The Recent Progress," Arch Pharm Res. Oct. 2002;25(5):572-84.

United States Patent and Trademark Office, Appeal 2008-3921, Application 101732,429. Technology Center 1600. Decided Mar. 5, 2009. Board Of Patent Appeals And Interferences Before Donald E. Adams, Richard M. Lebovitz, And Francisco C. Prats, Administrative Patent Judges, Ex Parte, Atul Varadhachary And Federica Pericle. 14 pages.

Indian First Examination Report issued Jul. 12, 2010 during prosecution of Indian Patent Application No. 3448/DELNP/2004.

Notification of Reasons for Refusal, issued Jan. 23, 2009 during the prosecution of Japanese Application No. 2004-506847.

NCI Issues Clinical Announcement for Preferred Method of Treatment for Advanced Ovarian Cancer: Questions and Answers http://www.cancer.gov/newscenter/pressreleases/IPchemotherapyQandA, (Apr. 10, 2008).

Kerbel, RS, (2003) Human Tumor Xenografts as Predictive Preclinical Models for Anticancer Drug Activity in Humans, Cancer Biology & Therapy 2:4:Suppl. S134-S139. (Apr. 10, 2008).

Radiation Therapy for Cancer: Questions and Answers http://www.cancer.gov/cancertopics/factsheet/Therapy/radiation (Apr. 10, 2008).

IND 11728-023 Annal Report - Cover Letter, (Jun. 7, 2004).

FDA correspondence regarding IND 11728, (Feb. 28, 2006).

* cited by examiner

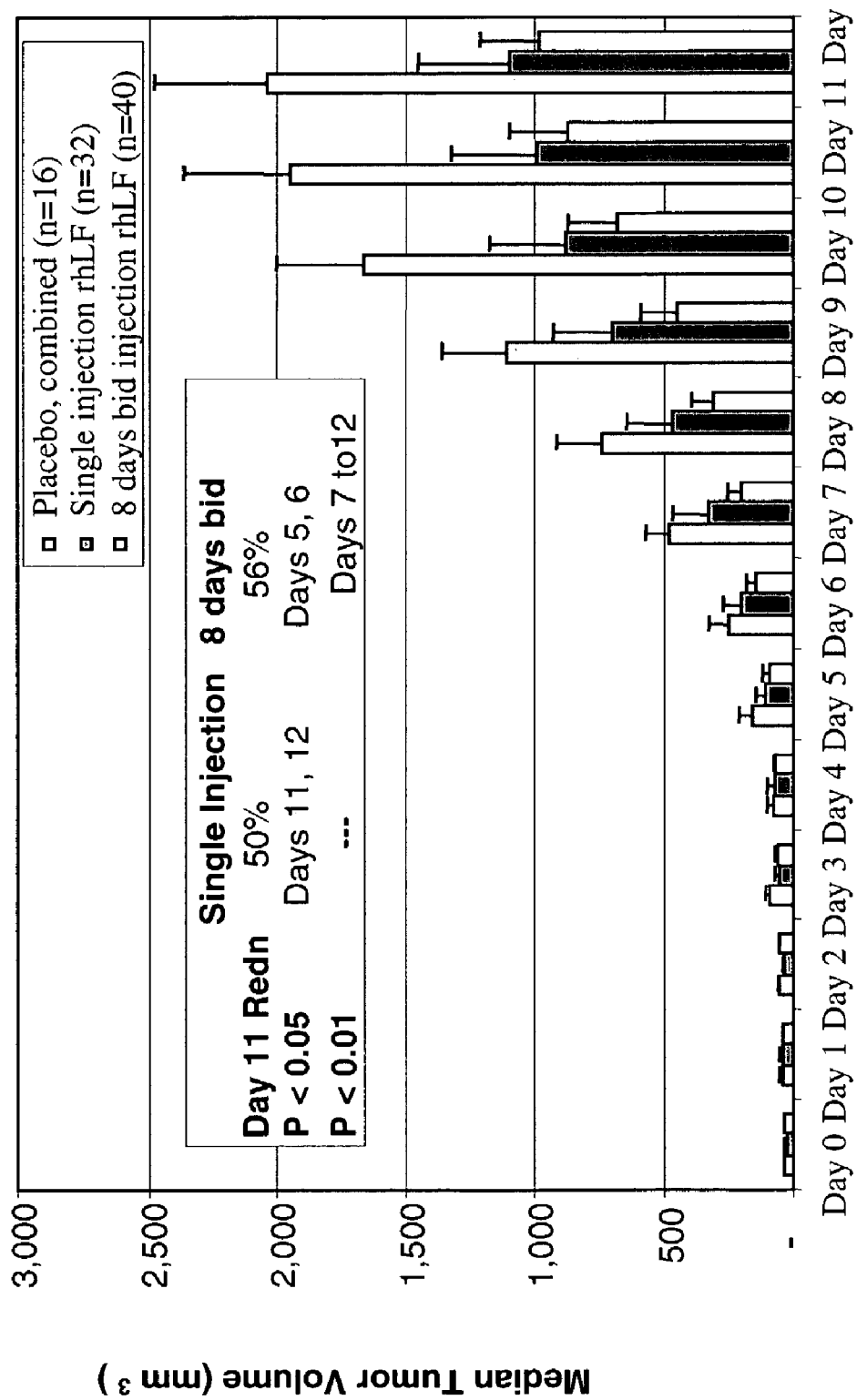

LACTOFERRIN IN THE TREATMENT OF MALIGNANT NEOPLASMS AND OTHER HYPERPROLIFERATIVE DISEASES

This application claims priority to U.S. Provisional Application No. 60/379,442 filed on May 10, 2002; U.S. Provisional Application No. 60/379,441 filed on May 10, 2002 and U.S. Provisional Application No. 60/379,474 filed on May 10, 2002, which are incorporated herein by reference in their entirety.

FIELD OF INVENTION

The present invention relates to methods of treating a hyperproliferative disease by administering a composition of lactoferrin alone or in combination with standard anti-cancer therapies. The lactoferrin composition may be administered orally, intravenously, intratumorally, or topically.

BACKGROUND OF THE INVENTION

Currently, there are few effective options for the treatment of many common cancer types. The course of treatment for a given individual depends on the diagnosis, the stage to which the disease has developed, and factors such as age, sex, and general health of the patient. The most conventional options of cancer treatment are surgery, radiation therapy, and chemotherapy. Surgery plays a central role in the diagnosis and treatment of cancer. Typically, a surgical approach is required for biopsy and the removal of cancerous growth. However, if the cancer has metastasized and is widespread, surgery is unlikely to result in a cure, and an alternate approach must be taken. Side effects of surgery include diminished structural or organ function and increased risk of infection, bleeding, or coagulation related complications. Radiation therapy, chemotherapy, biotherapy and immunotherapy are alternatives to surgical treatment of cancer (Mayer, 1998; Ohara, 1998; Ho et al., 1998). The disadvantage of many of the alternative therapies are the side effects, which can include myelosuppression, skin irritation, difficulty swallowing, dry mouth, nausea, diarrhea, hair loss, weight loss, and loss of energy (Curran, 1998; Brizel, 1998).

Lactoferrin is a single chain metal binding glycoprotein. Many cells types, such as monocytes, macrophages, lymphocytes, and intestinal brush-border cells, are known to have lactoferrin receptors. In addition to lactoferrin being an essential growth factor for both B and T lymphocytes, lactoferrin has a wide array of functions related to host primary defense mechanisms. For example, lactoferrin has been reported to activate natural killer (NK) cells, induce colony stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

Recently, bovine lactoferrin (bLF) was used as a prophylaxis for tumor formation and/or established tumors. The present invention is the first to use lactoferrin as a treatment, not a prophylaxis, for established tumors.

BRIEF SUMMARY OF THE INVENTION

The present invention is directed to a method for treating a hyperproliferative disease. The method of treatment involves oral, intravenous, topical and/or intratumoral administration of lactoferrin.

A specific embodiment of the present invention is a method of treating a hyperproliferative disease comprising the step of administering orally to a subject a human lactoferrin composition in an amount sufficient to provide an improvement in the hyperproliferative disease in the subject. More specifically, the amount of the composition that is administered is about 1 mg to about 100 g per day, more preferabley 20 mg to about 10 g per day. A further embodiment includes administering an antacid in conjunction with the human lactoferrin composition.

In specific embodiments, the human lactoferrin composition is dispersed in a pharmaceutically acceptable carrier. More specifically, the human lactoferrin is recombinant human lactoferrin.

The hyperproliferative disease is further defined as cancer, in which the cancer comprises a neoplasm. The neoplasm is selected from the group consisting of melanoma, non-small cell lung, small-cell lung, lung hepatocarcinoma, retinoblastoma, astrocytoma, gliobastoma, leukemia, neuroblastoma, squamous cell, head, neck, gum, tongue, breast, pancreatic, prostate, renal, bone, testicular, ovarian, mesothelioma, sarcoma, cervical, gastrointestinal, lymphoma, brain, colon, and bladder. More specifically, the neoplasm is a hematopoietic neoplasm. For example, the hematopoietic neoplasm is selected from the group consisting of acute myelogenous leukemia, acute lymphoblastic leukemia, myelodysplastic syndrome, chronic myelomonocytic leukemia, juvenile myelomonocyte leukemia, multiple myeloma, and chronic lymphocytic leukemia.

In further embodiments, the hyperproliferative disease is selected from the group consisting of rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, and psoriasis.

Another embodiment is a method of treating a hyperproliferative disease comprising the step of supplementing the mucosal immune system in a subject by increasing the amount of human lactoferrin in the gastrointestinal tract. The human lactoferrin is administered orally and stimulates the production of interleukin-18 and Granulocyte Macrophage Colony Stimulating Factor (GM-CSF).

Still further, another embodiment is a method of enhancing a mucosal immune response in the gastrointestinal tract in a subject comprising the step of administering orally to the subject a human lactoferrin. The human lactoferrin stimulates interleukin-18 and CM-CSF in the gastrointestinal tract. IL-18 stimulates the production, maturation, migration or activity of immune cells, e.g., T lymphocytes or natural killer cells. T lymphocytes are selected from the group consisting of CD4+, CD8+ and CD3+ cells. GM-CSF also stimulates the production, maturation, migration or activity of immune cells, e.g. dendritic cells and other antigen presenting cells. A further embodiment includes treating a hyperproliferative disease comprising administering orally to a subject a human lactoferrin composition in combination with chemotherapy, biotherapy, immunotherapy, surgery or radiotherapy. More particularly, the chemotherapy is a platinum based chemotherapy such as cisplatin or a taxane based chemotherapy such as docetaxel.

Another embodiment is a method of reducing growth of a neoplasm in a subject comprising the step of administering orally to the subject a human lactoferrin composition in an amount sufficient to reduce the growth of the neoplasm in the subject. Still further, the lactoferrin composition may be administered in combination with chemotherapy, biotherapy, immunotherapy, surgery or radiotherapy.

Still further, another embodiment is a method of treating a hyperproliferative disease comprising the step of administering intravenously to a subject a lactoferrin composition in an amount sufficient to provide an improvement in the hyperproliferative disease. The amount of the composition that is administered is about 0.1 µg to about 10 g per day. More particularly, the lactoferrin is mammalian lactoferrin, for example, human or bovine, and the lactoferrin can be recombinant lactoferrin.

Another embodiment comprises a method of treating a hyperproliferative disease comprising the step of supplementing a systemic immune system in a subject by increasing the amount of lactoferrin in the systemic circulation. The lactoferrin is administered intravenously. Still further, the lactoferrin composition is administered in combination with chemotherapy, biotherapy, immunotherapy, surgery or radiotherapy.

Still further, another embodiment is a method of enhancing a systemic immune response following the step of administering intravenously to the subject a lactoferrin composition. The lactoferrin stimulates interleukin-18 and GM-CSF. It is envisioned that interleukin-18 stimulates the production or activity of immune cells, for example T lymphocytes or natural killer cells and CM-CSF promotes the migration and maturation of immune cells including dendritic and other antigen presenting cells Still further, another embodiment is a method of treating a hyperproliferative disease comprising the step of administering topically to a subject a lactoferrin composition in an amount sufficient to provide an improvement in the hyperproliferative disease. The amount of the composition that is administered is about 0.1 µg to about 10 g per day. The composition may be a topical gel, a solution, capsule or a tablet having a lactoferrin concentration of about 0.01% to about 20%. More particularly, the lactoferrin is mammalian lactoferrin, for example, human or bovine, and the lactoferrin can be recombinant lactoferrin.

Another embodiment is a method of treating a hyperproliferative disease by topically administering a lactoferrin composition in combination with chemotherapy, biotherapy, immunotherapy, surgery or radiotherapy.

Still further, another embodiment is a method of enhancing a local or systemic immune response following the step of administering topically to the subject a lactoferrin composition. The lactoferrin stimulates production of interleukin-18 and/or GM-CSF by the keratinocytes. It is envisioned that interleukin-18 stimulates the production or activity of immune cells, for example T lymphocytes or natural killer cells and GM-CSF promotes the migration and maturation of immune cells including dendritic and other antigen presenting cells.

Yet further, another embodiment of the present invention is a method of stimulating, enhancing or up-regulating interleukin-18 and/or GM-CSF by administering a lactoferrin composition to a subject.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 5 shows squamous cell tumor growth with and without intratumoral administration of recombinant lactoferrin once or twice a day.

DETAILED DESCRIPTION OF THE INVENTION

Figure 1:
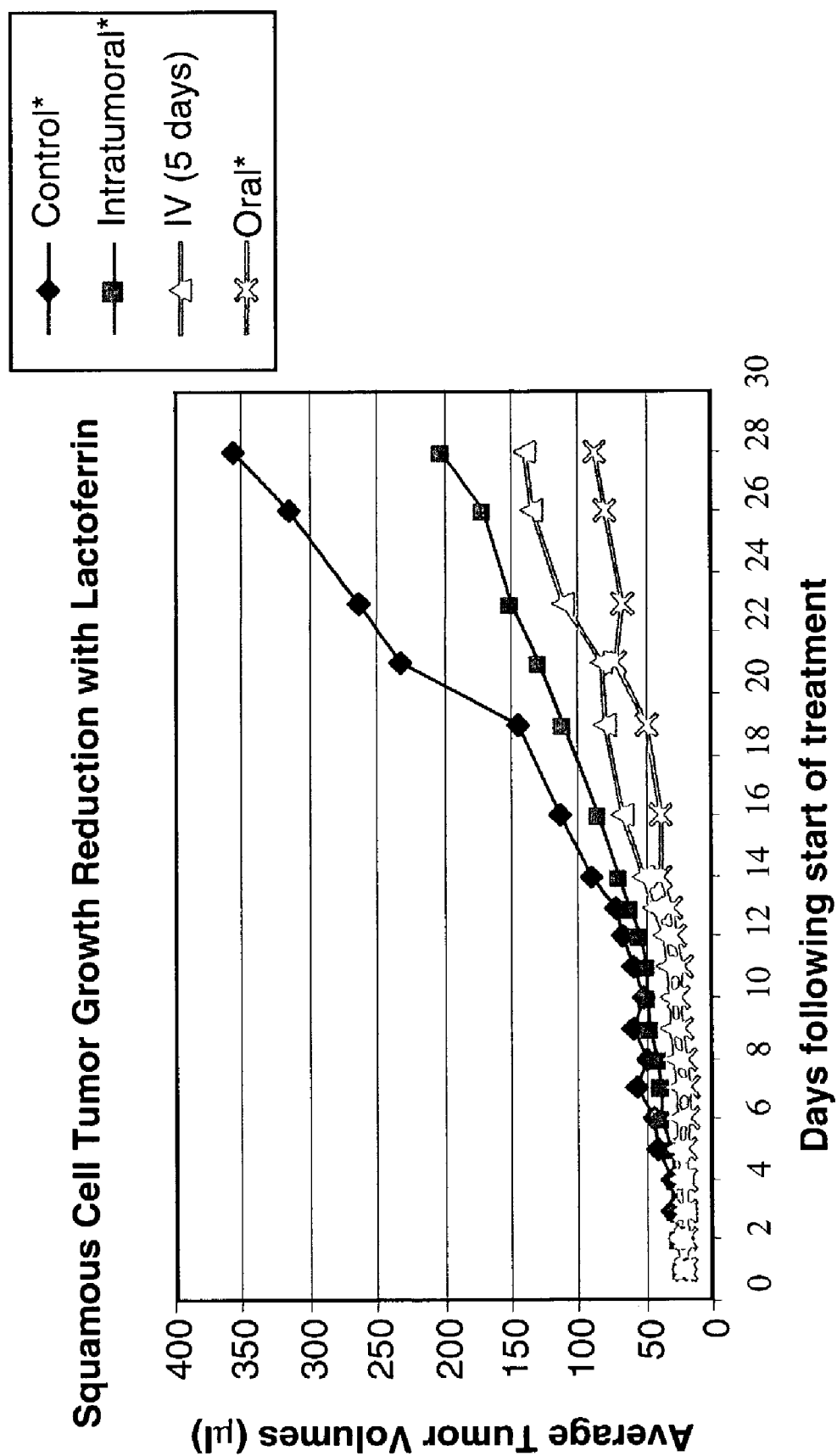
FIG. 1 shows squamous cell tumor growth with and without oral, intravenous and intratumoral administration of recombinant human lactoferrin.

It is readily apparent to one skilled in the art that various embodiments and modifications can be made to the invention disclosed in this Application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one."

The term "hyperproliferative disease" as used herein refers to any disease or disorder in which the cells proliferate more rapidly than normal tissue growth. Thus, a hyperproliferating cell is a cell that is proliferating more rapidly than normal cells.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intratumoral, intraocular, or intraarticular administration.

The term "intravenous administration" as used herein includes all techniques to deliver a lactoferrin composition to the systemic circulation via an intravenous injection or infusion.

The term "intratumoral administration" as used herein includes all techniques to deliver a lactoferrin composition to the site of a tumor including injection, electroporation, creams, lotions or other forms of administration.

The term "oral administration" as used herein includes oral, buccal, enteral or intragastric administration.

The term "topical administration" as used herein includes application to a dermal, epidermal, subcutaneous or mucosal surface.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "subject" as used herein, is taken to mean any mammalian subject to which the lactoferrin composition is administered according to the methods described herein. In a specific embodiment, the methods of the present invention are employed to treat a human subject. Another embodiment includes treating a human subject suffering from a hyperproliferative disease.

The term "therapeutically effective amount" as used herein refers to an amount that results in an improvement or remediation of the symptoms of the disease or condition.

The term "treating" and "treatment" as used herein refers to administering to a subject a therapeutically effective amount of a lactoferrin composition so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease. Specifically, improvements in patients with cancer may include tumor stabilization, tumor shrinkage, increased time to progression, increased survival or improvements in the quality of life. Beneficial effect may also be reflected in an improvement of the patient's immune system as measured by the number and activity of circulating immune cells such as CD4+ cells, CD8+ cells, NK cells and CD40+ cells.

The term "vicinity" as used herein refers to in or around the area or site of the tumor and/or hyperproliferative disease. For example, "vicinity of a tumor" may refer to the area in or around the tumor or margins of the tumor. Vicinity includes the area adjacent to the tumor, the area over the tumor, the area under the tumor, the margin area around the tumor, or the area adjacent the tumor margin area.

A. PHARMACEUTICAL COMPOSITIONS

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is human lactoferrin produced recombinantly using genetic engineering techniques well known and used in the art, such as recombinant expression or direct production in genetically altered animals, plants or eukaryotes, or chemical synthesis. See, i.e., U.S. Pat. Nos. 5,571,896; 5,571,697 and 5,571,691, which are herein incorporated by reference.

Administration of the lactoferrin compositions according to the present invention will be via any common route, orally, parenterally, or topically. Exemplary routes include, but are not limited to oral, nasal, buccal, rectal, vaginal, intramuscular, intraperitoneal, intravenous, intraarterial, intratumoral or dermal. Such compositions would normally be administered as pharmaceutically acceptable compositions as described herein.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the lactoferrin in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further in accordance with the present invention, the inventive composition suitable for oral administration is provided in a pharmaceutically acceptable carrier with or without an inert diluent. The carrier should be assimilable or edible and includes liquid, semi-solid, i.e., pastes, or solid carriers. Except insofar as any conventional media, agent, diluent or carrier is detrimental to the recipient or to the therapeutic effectiveness of a lactoferrin preparation contained therein, its use in an orally administrable lactoferrin for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, i.e., by solution, suspension, emulsification, admixture, encapsulation, microencapsulation, absorption and the like. Such procedures are routine for those skilled in the art.

In a specific embodiment of the present invention, the composition in powder form is combined or mixed thoroughly with a semi-solid or solid carrier. The mixing can be carried out in any convenient manner such as grinding. Stabilizing agents can be also added in the mixing process in order to protect the composition from loss of therapeutic activity through, i.e., denaturation in the stomach. Examples of stabilizers for use in an orally administrable composition include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like. More preferably, for an orally administered composition, the stabilizer can also include antagonists to the secretion of stomach acids.

Further, the composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, i.e., U.S. Pat. No. 5,629,001. Upon reaching the small intestines, the basic pH therein dissolves the coating and permits the composition to be released and absorbed by specialized cells, i.e., epithelial enterocytes and Peyer's patch M cells.

In another embodiment, a powdered composition is combined with a liquid carrier such as, i.e., water or a saline solution, with or without a stabilizing agent.

A specific formulation that may be used in the present invention is a solution of lactoferrin in a hypotonic phosphate based buffer that is free of potassium where the composition of the buffer is as follows: 6 mM sodium phosphate monobasic monohydrate, 9 mM sodium phosphate dibasic heptahydrate, 50 mM sodium chloride, pH 7.0±0.1. The concentration of lactoferrin in a hypotonic buffer may range from 10 microgram/ml to 100 milligram/ml. This formulation may be administered via any route of administration, for example, but not limited to intratumoral administration.

Further, a composition for topical administration which is combined with a semi-solid carrier can be further formulated into a gel ointment. A preferred carrier for the formation of a gel ointment is a gel polymer. Preferred polymers that are used to manufacture a gel composition of the present invention include, but are not limited to carbopol, carboxymethylcellulose, and pluronic polymers. Specifically, a powdered lactoferrin composition is combined with an aqueous gel containing an polymerization agent such as Carbopol 980 at strengths between 0.5% and 5% wt/volume for application to the skin for treatment of hyperproliferative disease on or beneath the skin.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

B. TREATMENT OF HYPERPROLIFERATIVE DISEASES

In accordance with the present invention, a lactoferrin composition provided in any of the above-described pharmaceutical carriers is administered to a subject suspected of or having a hyperproliferative disease. One of skill in the art can determine the therapeutically effective amount of human lactoferrin to be administered to a subject based upon several considerations, such absorption, metabolism, method of delivery, age, weight, disease severity and response to the therapy.

The route of administration will vary, naturally, with the location and nature of the lesion, and include, for example intradermal, transdermal, parenteral, intravenous, intramuscular, intranasal, subcutaneous, percutaneous, intratracheal, intraperitoneal, intratumoral, perfusion, lavage, direct injection, and oral administration.

Oral administration of the lactoferrin composition includes oral, buccal, enteral or intragastric administration. It is also envisioned that the composition may be used as a food additive. For example, the composition is sprinkled on food or added to a liquid prior to ingestion.

Intratumoral administration of the lactoferrin composition includes intratumoral injection, electroporation, or surgical or endoscopic implantation. Intratumoral injection, or injection into the tumor vasculature is specifically contemplated for discrete, solid, accessible tumors. Local, regional or systemic administration also may be appropriate.

The hyperproliferative disease, includes but is not limited to neoplasms. A neoplasm is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias, lymphomas and myelomas. A tumor is the neoplastic growth of the disease cancer. As used herein, a "neoplasm", also referred to as a "tumor", is intended to encompass hematopoietic neoplasms as well as solid neoplasms. Examples of neoplasms include, but are not limited to melanoma, non-small cell lung, small-cell lung, lung, hepatocarcinoma, retinoblastoma, astrocytoma, gliobastoma, gum, tongue, leukemia, neuroblastoma, head, neck, breast, pancreatic, prostate, renal, bone, testicular, ovarian, mesothelioma, sarcoma, cervical, gastrointestinal, lymphoma, brain, colon, bladder, myeloma, or other malignant or benign neoplasms.

Other hyperproliferative diseases include, but are not limited to neurofibromatosis, rheumatoid arthritis, Waginer's granulomatosis, Kawasaki's disease, lupus erathematosis, midline granuloma, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis, and pre-leukemias, anemia with excess blasts, and myelodysplastic syndrome.

Particular neoplasms of interest in the present invention include, but are not limited to hematopoietic neoplasms. For example, a hematopoietic neoplasm may include acute myelogenous leukemia, acute lymphoblastic leukemia, myelodysplastic syndrome, chronic myelomonocytic leukemia, juvenile myelomonocyte leukemia, multiple myeloma, chronic lymphocytic leukemia or other malignancy of hematologic origin.

In a preferred embodiment of the present invention, the lactoferrin compositions are administered in an effective amount to decrease, reduce, inhibit or abrogate the growth of a tumor. The amount may vary from about 0.1 µg to about 100 g of the lactoferrin composition. Preferably, the lactoferrin composition is orally administered in the range of 1 mg to 100 g per day, more preferably about 20 mg to about 10 g per day with the most preferred dose being 4.5 g per day. Intravenously administered lactoferrin can be in the range of 0.1 µg to about to 10 g per day, more preferably about 0.1 µg to about 1 mg with the most preferred dose being 250 mg per day. Preferably, a lactoferrin composition is intratumorally administered in the range of 0.1 µg to 10 g per day with the most preferred dose being 100 µg per day. Topically, the amount of lactoferrin may vary from about 1 µg to about 100 g of lactoferrin. Preferably, the topical gel, solution, capsule or tablet comprises a lactoferrin concentration of about 0.01% to about 20%. More preferably, the topical gel, solution, capsule or tablet may comprise a lactoferrin concentration of about 1% to about 8.5%.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with the lactoferrin composition may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

Alternatively, the present invention may be used at the time of surgery, and/or thereafter, to treat residual or metastatic disease. For example, a resected tumor bed may be injected or perfused with a formulation comprising the lactoferrin composition. The perfusion may be continued post-resection, for example, by leaving a catheter implanted at the site of the surgery. Periodic post-surgical treatment is also envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs. It was further contemplated that limb perfusion may be used to administer therapeutic compositions of the present invention, particularly in the treatment of melanomas and sarcomas.

In specific embodiments, the lactoferrin composition is given in a single dose or multiple doses. The single dose may be administered daily, or multiple times a day, or multiple times a week, or monthly or multiple times a month. In a further embodiment, the lactoferrin composition is given in a series of doses. The series of doses may be administered daily, or multiple times a day, weekly, or multiple times a week, or monthly, or multiple times a month.

A further embodiment of the present invention is a method of treating a hyperproliferative disease comprising the step of supplementing a mucosal immune system by increasing the amount of lactoferrin in the gastrointestinal tract. Preferably, the lactoferrin is administered orally.

Still yet, a further embodiment is a method of enhancing a mucosal immune response in the gastrointestinal tract in a subject comprising the step of administering orally to said subject a lactoferrin composition, preferably human lactoferrin. It is envisioned that lactoferrin stimulates interleukin-18 and GM-CSF in the gastrointestinal tract, which enhance immune cells. For example, interleukin-18 enhances T lymphocytes or natural killer cells and GM-CSF promotes maturation and migration of immune cells including dendritic and other antigen presenting cells. In specific embodiments, interleukin-18 (IL-18) enhances CD4+, CD8+ and CD3+ cells. It is known by those of skill in the art that IL-18 is a Th1 cytokine that acts in synergy with interleukin-12 and interleukin-2 in the stimulation of lymphocyte IFN-gamma production. Other cytokines may also be enhanced for example, but not limited to IL-1b or, IL-12 or IFN-gamma. It is also envisioned that lactoferrin stimulates interleukin-18 following oral administration, which inhibits angiogenesis and thereby has activity against tumor cells which are dependent on neovascularization.

A further embodiment of the present invention is a method of treating a hyperproliferative disease comprising the step of supplementing the systemic immune system by increasing the amount of lactoferrin in the systemic circulation. Preferably, the lactoferrin composition is administered intravenously. It is envisioned that lactoferrin stimulates interleukin-18 and GM-CSF in the tissue, which enhance immune cells. For example, interleukin-18 enhances T lymphocytes or natural killer cells and GM-CSF promotes maturation and migration of immune cells including dendritic and other antigen presenting cells. In specific embodiments, interleukin-18 (IL-18) enhances CD4+, CD8+ and CD3+ cells. It is known by those of skill in the art that IL-18 is a Th1 cytokine that acts in synergy with interleukin-12 and interleukin-2 in the stimulation of lymphocyte IFN-gamma production. Other cytokines may also be enhanced for example, but not limited to IL-1b or, IL-12 or IFN-gamma. It is also envisioned that lactoferrin stimulates interleukin-18 following intravenous administration, which inhibits angiogenesis and thereby has activity against tumor cells which are dependent on neovascularization.

A further embodiment of the present invention is a method of treating a hyperproliferative disease comprising the step of supplementing a local or systemic immune system by increasing the amount of lactoferrin in the vicinity of the tumor. Vicinity of the tumor refers to the general area of the tumor, for example the lactoferrin can be administered directly into or on the tumor, or in the general area of the tumor, but not directly into the tumor. The general area may include the margin area or near or adjacent the margin area of the tumor. Preferably, the lactoferrin composition is administered intratumorally. It is envisioned that lactoferrin stimulates interleukin-18 and GM-CSF in the local tissue, which enhances immune cells. For example, interleukin-18 enhances T lymphocytes or natural killer cells and GM-CSF promotes maturation and migration of immune cells including dendritic and other antigen presenting cells. In specific embodiments, interleukin-18 (IL-18) enhances CD4+, CD8+ and CD3+ cells. It is known by those of skill in the art that IL-18 is a Th1 cytokine that acts in synergy with interleukin-12 and interleukin-2 in the stimulation of lymphocyte IFN-gamma production. Other cytokines may also be enhanced for example, but not limited to IL-1b or, IL-12 or IFN-gamma. It is also envisioned that lactoferrin stimulates interleukin-18 following intratumoral administration, which inhibits angiogenesis and thereby has activity against tumor cells which are dependent on neovascularization.

A further embodiment of the present invention is a method of treating a hyperproliferative disease comprising the step of supplementing a local or systemic immune system by increasing the amount of lactoferrin in the skin in the vicinity of the tumor. Preferably, the lactoferrin composition is administered topically. As above, administration in the vicinity of the tumor includes administration near or adjacent to the margins of the tumor or directly in the margin area of the tumor. It is envisioned that lactoferrin stimulates interleukin-18 and GM-CSF in the local tissue (e.g., keratinocytes), which enhances immune cells. For example, interleukin-18 enhances T lymphocytes or natural killer cells and GM-CSF promotes maturation and migration of immune cells including dendritic and other antigen presenting cells. In specific embodiments, interleukin-18 (IL-18) enhances CD4+, CD8+ and CD3+ cells. It is known by those of skill in the art that IL-18 is a Th1 cytokine that acts in synergy with interleukin- 12 and interleukin-2 in the stimulation of lymphocyte IFN-gamma production. Other cytokines may also be enhanced for example, but not limited to IL-1b or, IL-12 or IFN-gamma. It is also envisioned that lactoferrin stimulates interleukin-18 following intratumoral administration, which inhibits angiogenesis and thereby has activity against tumor cells which are dependent on neovascularization.

C. COMBINATION TREATMENTS

In order to increase the effectiveness of the human lactoferrin composition of the present invention, it may be desirable to combine the composition of the present invention with other agents effective in the treatment of hyperproliferative disease, such as anti-cancer agents, or with surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve administering the human lactoferrin composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the human lactoferrin composition and the other includes the second agent(s).

Alternatively, the lactoferrin composition of the present invention may precede or follow the other anti-cancer agent treatment by intervals ranging from minutes to weeks. In embodiments where the other anti-cancer agent and lactoferrin composition are administered or applied separately to the cell, one would generally ensure that a significant period of time did not expire between the time of each delivery, such that the agent and lactoferrin composition would still be able to exert an advantageously combined effect on the cell. In such instances, it is contemplated that one may contact the cell with/administer both modalities within about 1-14 days of each other and, more preferably, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

1. Chemotherapy

Cancer therapies also include a variety of chemical based treatments. Some examples of chemotherapeutic agents include without limitation antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as TAXOL® (paclitaxel), Vincristine, Vinblastine, miscellaneous agents such as platinum based agents (e.g., Cisplatin (CDDP)), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, (a phenylalanine derivative of nitrogen mustard), Cyclophosphamide, Chlorambucil, Busulfan (also known as myleran), taxane based agents (e.g., docetaxel) and Lomustine.

Some examples of other agents include, but are not limited to, Carboplatin, Procarbazine, Mechlorethamine, Irinotecan, Topotecan, Ifosfamide, Nitrosurea, Etoposide (VP16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabine, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

2. Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage to DNA, the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

3. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

4. Other Biotherapy Agents

It is contemplated that other biological agents may be used in combination with the present invention to improve the therapeutic efficacy of treatment. These additional agents include, without limitation, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents, as well as biotherapy such as for example, hyperthermia.

Hyperthermia is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

5. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

It is contemplated that vaccines that are used to treat cancer may be used in combination with the present invention to improve the therapeutic efficacy of the treatment. Such vaccines include peptide vaccines or dendritic cell vaccines. Peptide vaccines may include any tumor-specific antigen that is recognized by cytolytic T lymphocytes. Yet further, one skilled in the art realizes that dendritic cell vaccination comprises dendritic cells that are pulsed with a peptide or antigen and the pulsed dendritic cells are administered to the patient.

Examples of tumor-specific antigens that are being used as vaccines in melanoma include, but are not limited to gp100 or MAGE-3. These antigens are being administered as peptide vaccines and/or as dendritic cell vaccines.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Inhibition of Tumor Growth by RhLF

Human squamous cell carcinoma (O12) was used. The cells were injected into the right flank of athymic nude mice. rhLF was administered either intratumorally (49 animals, 7 doses ranging from 0.05 μg to 125 μg per dose), intravenously (7 animals, 125 ug/dose) or orally (7 animals 20 mg/dose). Control animals were treated with only the vehicle; no rhLF was administered to the control animals. rhLF was administered twice a day for either five days (intravenous group) or eight days (all other groups) starting 11 days after inoculation with tumor cells to allow formation of established tumors.

The efficacy of treatment was evaluated by measuring the solid tumor size during and at the end of the experiment; the body weights were also determined at the time of tumor measurements. As seen in FIG. 1 and Table 1, treatment with rhLF reduced rates of tumor growth relative to the control by 46% to 80%. In fact, oral treatment with 20 mg rhLF most significantly reduced the tumor growth, by 80% compared to the control ($p=0.0073$).

TABLE 1

Summary of tumor growth inhibition by rhLF in O12 tumor model in mice

| | Inhibition Relative to Placebo | | P value | |
|---|---|---|---|---|
| | Day 19* | Day 28* | Day 19* | Day 28* |
| Intratumoral N = 49 | 28% | 46% | 0.139 | 0.0263** |
| Intravenous N = 7 | 55% | 65% | 0.0666 | 0.0233** |
| Oral N = 7 | 76% | 80% | 0.0175** | 0.0073*** |

*following start of treatment
**statistically significant ($p < 0.05$)
***highly statistically significant ($p < 0.01$)

Results from this study showed that rhLF administered by multiple routes significantly inhibited tumor growth in a squamous cell tumor model in mice, with oral administration being the most effective. Based upon these results, it was further contemplated that oral lactoferrin affects the tumor by enhancing immune cell activity.

Example 2

Evaluation of RhLF in Tumor Types

Tumor cells from a broad range of tumor types are injected into the right flank of athymic nude mice. Animals are administered either rhLF, native hLF or bovine LF orally. Control animals are treated with only the vehicle, no rhLF is administered to the control animals. rhLF is administered either once or twice a day for either one, five, seven or fourteen days or eight days starting approximately eleven days after inoculation with tumor cells to allow formation of established tumors or at such other time as is generally done with standard or published regimens.

The efficacy of treatment is evaluated by measuring the solid tumor size during and at the end of the experiment; the body weights are also determined at the time of tumor measurements. The immune response is measured by measuring the amount of cytokines, T-cells and NK cells in circulation and in the intestine.

Example 3

Effect of Oral Administration of RhLF and bLF

Recombinant human lactoferrin and bovine lactoferrin were orally administered to mice, and the production of IL-18 in the small intestine was measured.

Mice were treated for three days daily with 65 mg/kg/day of rhLF, 300 mg/kg/day of rhLF or 300 mg/kg/day of bLF. For a control, mice were only administered the pharmaceutical carrier. Twenty-four hours following administration of the LF or control for 3 days, animals were weighed and blood and serum were collected. Serum was used for cytokine ELISA assays.

Also, at these time points, animals were sacrificed and the small intestinal tissue was removed for further analysis. Small intestinal epithelium was homogenized using a lysis buffer consisting of PBS, 1% Nonidet P-40, 0.5% sodium deoxycholate, and 0.1% sodium dodecyl sulphate containing 10 µg/ml PhenylMetheylsulfonyl fluoride. Homogenate was centrifuged at 15,000 rpm for 10 minutes and the supernatant stored at −80 C. till it was tested for IL-18 levels.

As seen in Table 2 and Table 3, administration of rhLF at both doses significantly enhanced the amounts of IL-18 in both the serum and in the intestinal extract. Bovine LF caused a lesser increase in the intestinal IL-18 levels and did not increase the serum levels of IL-18.

TABLE 2

Effect of rhLF and bLF on IL-18 levels in the gut and serum

|  | Intestinal Extract (pg) | Serum (pg) |
| --- | --- | --- |
| Control | 955 | 141 |
| 300 mg/kg bLF | 4,515 | 134 |
| 65 mg/kg rhLF | 7,879 | 259 |
| 300 mg/kg rhLF | 8,350 | 328 |

TABLE 3

Stimulation by rhLF and bLF of IL-18 levels in the gut and serum

|  | Intestinal Extract % Increase | P-value | Serum % Increase | P-value |
| --- | --- | --- | --- | --- |
| Increase Over Control |  |  |  |  |
| 300 mg/kg bLF | 373% | 0.0086 | −5% | 0.5411 |
| 65 mg/kg rhLF | 725% | 0.0034 | 84% | 0.0132 |
| 300 mg/kg rhLF | 775% | 0.0001 | 132% | 0.0007 |
| Increase Over Blf |  |  |  |  |
| 65 mg/kg rhLF | 75% | 0.1490 | 94% | 0.0366 |
| 300 mg/kg rhLF | 85% | 0.0617 | 145% | 0.0084 |

Example 4

Effect of Oral RhLF on NK Activity In Vivo

Balb/c naïve mice were treated orally with rhLF or placebo once a day for 3 days (see Table 4).

TABLE 4

Treatment Regimen

| Treatment* | N | Dose (mg/kg) | Route | Schedule |
| --- | --- | --- | --- | --- |
| Group 1 Placebo | 6 | 0 | — | — |
| Group 2 RhLF | 7 | 300 mg/kg/day | Oral | 3 days |

On day 4, mice were sacrificed and spleens were collected. NK cells were separated using a magnetic bead cell sorting assay (MACS anti-NK-DX5) and counted. Cells were then tested in vitro for NK-activity against YAC targets using a lactate dehydrogenase (LDH) release test.

Table 5 shows that oral rhLF treatment resulted in a significant increase of NK activity ex-vivo against YAC-target cells (10% @ 30:1 versus 2.8% of ctrl group). No significant change in NK activity was observed in placebo treated mice.

TABLE 5

NK activity in mice treated with oral rhLF

| Control | | |
| --- | --- | --- |
| Low | Medium | High |
| 0.056 | 0.09 | 0.407 |

| | Placebo | | | | RhLF-treated | | | |
| --- | --- | --- | --- | --- | --- | --- | --- | --- |
| | Raw data | | | | Raw data | | | |
| | E:T | | | | E:T | | | |
| E:T ratio | cell mix | E cell ctrl | % Cytotoxicity* Final | | cell mix | E cell ctrl | Final | % Cytotoxicity* Increased over ctrl |
| 30:1 | 0.281 | 0.215 | 2.86 | | 0.358 | 0.267 | 9.81 | 7** |
| 15:1 | 0.176 | 0.110 | 2.85 | | 0.214 | 0.143 | 4.12 | 1.3 |
| 7.5:1 | 0.117 | 0.054 | 2.21 | | 0.131 | 0.074 | 0.44 | 0 |
| 3.7:1 | 0.086 | 0.030 | 0.19 | | 0.096 | 0.042 | 0 | 0 |

*% Cytotoxicity = [(Effector:target cell mix − effectors cell ctrl)] − low ctrl/[(high ctrl − low ctrl)] × 100
**p < 0.05 ((2-tailed p value)

Example 5

Effect of Oral Administration of RhLF on GM-CSF In Vivo

Recombinant human lactoferrin or placebo were orally administered to mice, and the production of GM-CSF in the small intestine was measured.

Mice (5 animals per group) were treated for three days daily with 300 mg/kg/day of rhLF. For a control, mice were only administered the pharmaceutical carrier. Twenty-four hours following administration of the LF or placebo for 3 days, animals were and the small intestinal tissue was removed for further analysis. Small intestinal epithelium was homogenized using a lysis buffer consisting of PBS, 1% Nonidet P-40, 0.5% sodium deoxycholate, and 0.1% sodium dodecyl sulphate containing 10 µg/ml PhenylMetheylsulfonyl fluoride. Homogenate was centrifuged at 15,000 rpm for 10 minutes and the supernatant stored at −80 C. till it was tested for GM-CSF levels using an ELISA kit.

As shown in Table 6, treatment with rhLF increased the production of a key immunostimulatory cytokine, GM-CSF, in the small intestine relative to the placebo treated animals.

TABLE 6

Effect of rhLF on GM-CSF levels in the gut and serum

|  | Mean (SEM) in pg | Increase over Placebo |
|---|---|---|
| Placebo | 6.48 (0.32) | — |
| 300 mg/kg rhLF | 7.74 (0.19) | 19.4% (p < 0.01) |

Example 6

Combination of hLF with Chemotherapy

A murine squamous carcinoma cell line (SCCVII) was injected into the floor of the mouth through the neck skin of immunocompetent C3H mice (Day 0). Five days after tumor cell implantation (Day 5), a skin incision was made in the lower neck and surgical dissection revealed the established tumors. Tumors were measured in three dimensions with calipers.

Tumor-bearing mice were randomized into a control group and seven groups receiving rhLF and/or cisplatin. RhLF (4 mg; 200 mg/Kg) was administered once daily by oral gavage for 8 days on days 5 through 12. Cisplatin was administered as a single dose of 5 mg/Kg given intraperitoneally either at the start of rhLF (day 5), in the middle (day 8) or at the end (day 12) of rhLF therapy. Animals were sacrificed on day 12 post-implantation and the residual tumor masses were measured and processed for later additional analyses.

TABLE 7

Experimental Groups

|  | Description | N | RhLF mg/kg | Cisplatin |
|---|---|---|---|---|
| Group A | Placebo | 5 | 0 (Placebo) | 0 |
| Group B | RhLF Alone | 5 | 200 mg/kg | 0 |
| Group C | CP Day 5 | 5 | 0 | 5 mg/kg on day 5* |
| Group D | CP Day 8 | 5 | 0 | 5 mg/kg on day 8* |
| Group E | CP Day 12 | 4 | 0 | 5 mg/kg on day 12 |
| Group F | RhLF/CP-5 | 5 | 200 mg/kg | 5 mg/kg on day 5* |
| Group G | RhLF/CP-8 | 5 | 200 mg/kg | 5 mg/kg on day 8* |
| Group H | RhLF/CP-12 | 5 | 200 mg/kg | 5 mg/kg on day 12* |

Figure 2:
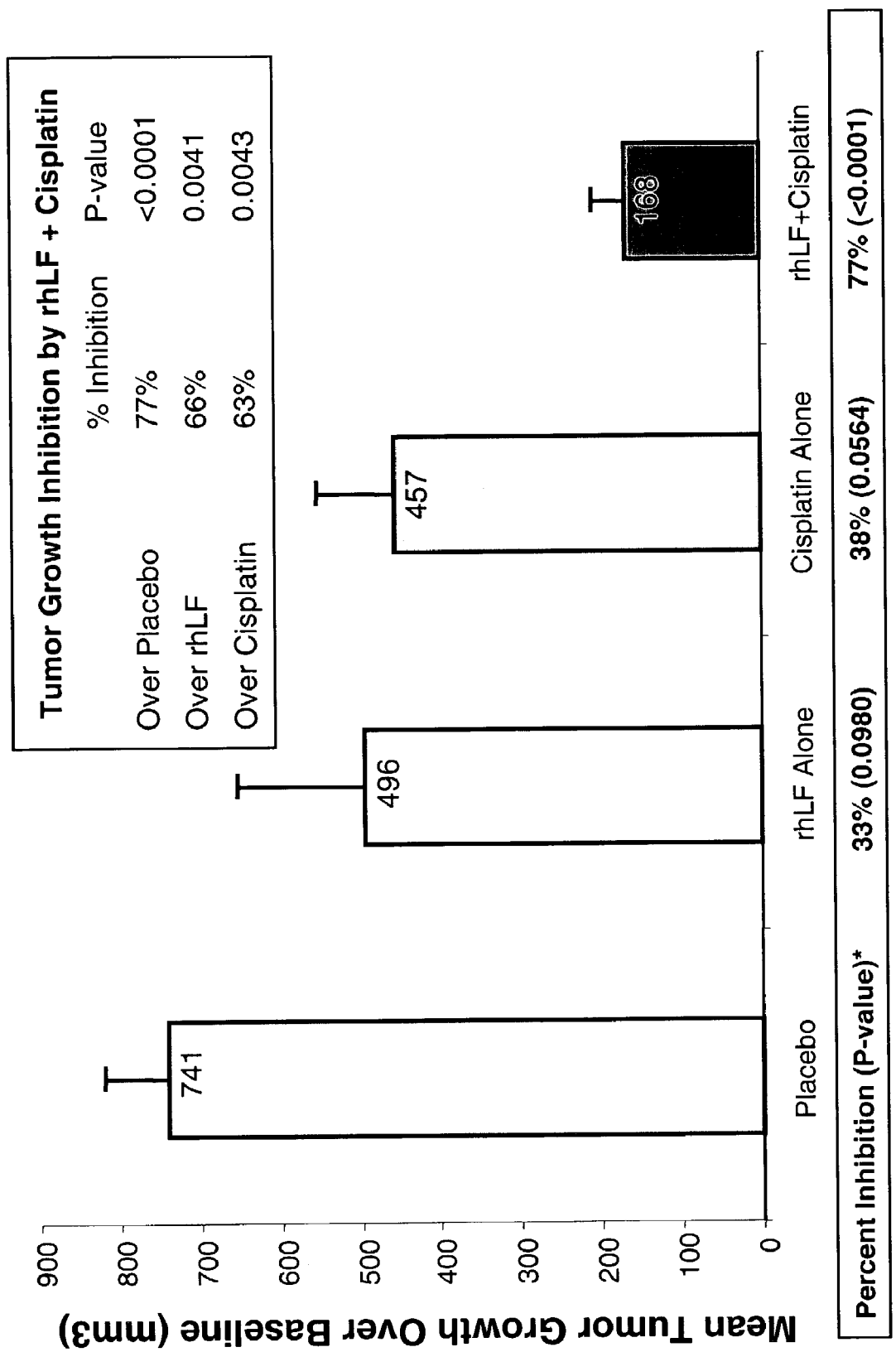
FIG. 2 shows percent tumor growth inhibition in animals receiving lactoferrin, cisplatin and lactoferrin in combination with cisplatin.

Mice treated either with rhLF alone, cisplatin alone or both agents, showed a tumor growth inhibition (TGI) relative to the placebo animals. The maximum inhibition was observed in the group receiving both therapies (Table 7 and FIG. 2).

In all cases, the animals receiving rhLF+cisplatin showed a TGI relative to the relevant group receiving cisplatin alone. When pooled for analysis, animals receiving rhLF+cisplatin showed a 77% TGI relative to the placebo animals (P<0.0001), a 66% TGI relative to rhLF alone (P<0.01) and a 63% TGI relative to cisplatin alone (P<0.01).

Cisplatin dosing immediately prior to the start of rhLF (RhLF+CP-5) or during the period of rhLF administration (RhLF+CP-8) provided greater incremental benefit than when cisplatin was administered following completion of rhLF therapy (RhLF+CP-12). However, only the straddling regimen (RhLF+CP-8) provided a statistically significant improvement (P<0.01) TGI of 77% over cisplatin alone (CP Day 8).

TABLE 8

Tumor Growth Inhibition (TGI) by Treatment Group

| Group | Growth (SEM) | Relative to Placebo* TGI (%) | P-value |
|---|---|---|---|
| A (Placebo) | 741 (79) | — | — |
| B (RhLF alone) | 496 (155) | 33% | 0.0989 |
| C (CP Day 5) | 240 (137) | 68% | 0.0066 |
| D (CP Day 8) | 693 (146) | 6% | 0.3898 |
| E (CP Day 12) | 433 (175) | 42% | 0.0634 |
| F (RhLF + CP-5) | 14 (5) | 98% | <0.0001 |
| G (RhLF + CP-8) | 159 (48) | 79% | 0.0001 |
| H (RhLF + CP-12) | 331 (47) | 55% | 0.0011 |
| C to E (All CP) | 457 (96) | 38% | 0.0564 |
| F to H (All rhLF/CP) | 168 (40) | 77% | <0.0001 |

*Inhibition and 1-tailed P-value relative to the placebo group
**Inhibition and 1-tailed P-value compared to the respective Cisplatin groups

Example 7

Dose Dependence of Combining hLF with Chemotherapy

Figure 3:
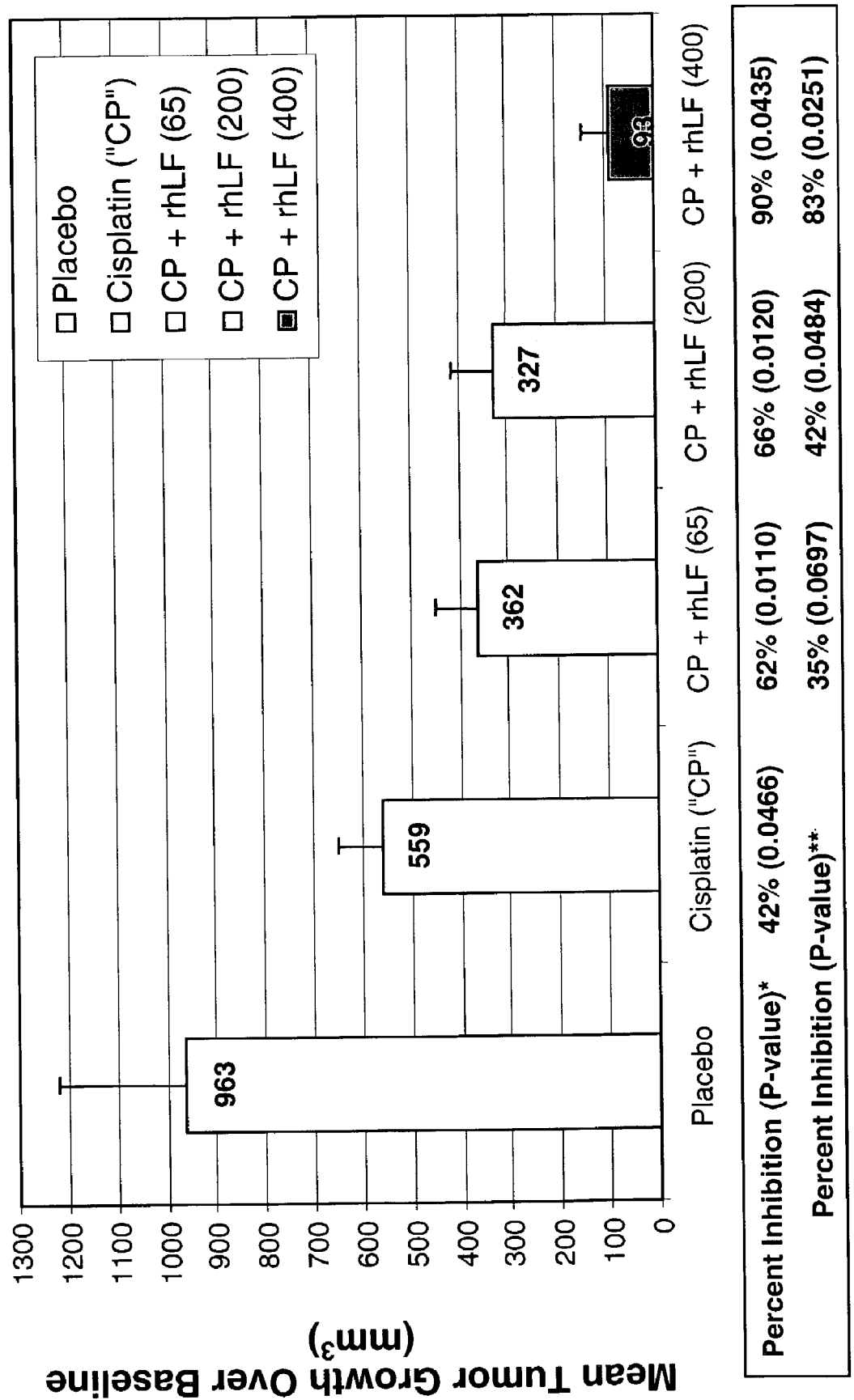
FIG. 3 shows the percent tumor growth inhibition with lactoferrin in combination with various doses of cisplatin.

A murine squamous carcinoma cell line (SCCVII) was injected into the floor of the mouth through the neck skin of immunocompetent C3H mice (Day 0) as described in Example 6. On Day 5 days after initial implantation, tumors were measured for the baseline, then treated with either cisplatin (Day 8, i.p., 5 mg/kg) alone or cisplatin plus three doses of oral rhLF (daily by gavage for 7-8 days on days 5 through 11/12). Animals were sacrificed on Day 11/12 and tumors measured. There was a dose dependent inhibition of tumor growth in the animals receiving both rhLF and cisplatin as compared to the animals receiving cisplatin alone as shown in FIG. 3.

Example 8

Combination of hLF with Docetaxel

A murine squamous carcinoma cell line (SCCVII) was injected into the floor of the mouth through the neck skin of immunocompetent C3H mice (Day 0) as described in Example 7. On Day 5 after initial implantation, tumors were measured for the baseline, then treated with either oral placebo alone (once daily from days 5 to 12; 6 animals), placebo and docetaxel (i.v. bolus of 31.3 mg/kg docetaxel on Day 8; 9 animals), or docetaxel plus oral rhLF (200 mg/kg, administered once daily by gavage from days 5 to 12; 9 animals). Animals were sacrificed on Day 14 and tumors measured. Docetaxel alone caused an inhibition of tumor growth relative to placebo and the combination of rhLF and docetaxel induced a further growth inhibition. Inhibition and p-values (1-tailed) are shown in Table 9.

TABLE 9

Tumor Growth Inhibition (TGI) by Treatment Group

| Group | Growth (SEM) | Relative to Placebo* TGI (%) | P-value | Relative to Docetaxel TGI (%) | P-value |
|---|---|---|---|---|---|
| Placebo | 5,157 (497) | — | — | — | — |
| Docetaxel | 2,103 (209) | 59% | <0.0001 | — | — |
| Docetaxel + rhLF | 1,288 (286) | 75% | <0.0001 | 39% | 0.0175 |

Example 9

Combination of hLF with Radiotherapy

A murine squamous carcinoma cell line (SCCVII) was injected into the floor of mouth through the neck skin of immunocompetent C3H mice (Day 0). Five days after tumor cell implantation (Day 5), a skin incision was made in the lower neck and surgical dissection revealed the established tumors. Tumors were measured in three dimensions with calipers.

Tumor-bearing mice were randomized into six groups receiving rhLF (200 mg/Kg) and/or radiotherapy as described below. RhLF (4 mg; 200 mg/kg) was administered by oral gavage once daily for 8 days on days 5 through 12. Radiotherapy was administered as single dose of 2 Gray given at the beginning (day 5) or at during (day 8) rhLF-therapy. Animals were sacrificed on day 14 post-treatment and the residual tumor masses were measured and processed for later additional analyses.

TABLE 10

Experimental Groups

| | Description | N | RhLF mg/kg* | Radiation |
|---|---|---|---|---|
| Group A | Placebo | 10 | 0 (Placebo) | None |
| Group B | RhLF Alone | 10 | 200 mg/kg | None |
| Group C | Radiation Day 5 | 8 | 0 | 2 Gray on day 5 |
| Group D | RhLF/Rad 5 | 10 | 200 mg/Kg | 2 Gray on day 5 |
| Group E | Radiation Day 8 | 10 | 0 | 2 Gray on day 8 |
| Group F | RhLF/Rad 8 | 10 | 200 mg/kg | 2 Gray on day 8 |

*RhLF/placebo was administered once daily by oral gave from Days 5 to 12.

Mice receiving rhLF alone, radiotherapy alone, or combination therapy showed a significant tumor growth inhibition (TGI) relative to placebo treated mice. The mice receiving both rhLF and radiation showed a modest increase in TGI over monotherapy with rhLF (28%, $P<0.05$) and radiation (15%, $P=0.1207$).

TABLE 11

Tumor Growth Inhibition (TGI) by Treatment Group:

| | Growth | Relative to Placebo | |
|---|---|---|---|
| Group | (SEM) | Inhibition* | P-value* |
| A (Placebo) | 2348 (395) | — | |
| B (rhLF alone) | 1074 (163) | 54% | 0.0040 |
| C (Radiation Day 5) | 827 (105) | 65% | 0.0021 |
| D (rhLF/Rad 5) | 750 (125) | 68% | 0.0006 |
| E (Radiation Day 8) | 977 (112) | 58% | 0.0018 |
| F (rhLF/Rad 8) | 797 (119) | 66% | 0.0007 |
| C/E (Both Radiation) | 911 (78) | 61% | <0.0001 |
| D/F (Both rhLF/Rad) | 774 (84) | 67% | <0.0001 |

*Inhibition and 1-tailed P-value compared to the placebo group

Thus, lactoferrin stimulated the immune system. Still further, lactoferrin in combination with cisplatin, docetaxel and/or radiation resulted in inhibition of tumor growth.

Example 10

Oral Administration of hLF in Humans

Recombinant human lactoferrin was orally administered to human patients with a range of metastatic cancer types that had failed standard chemotherapy in two different studies conducted in multiple centers in four countries (Argentina, Brazil, Chile, U.S.) RhLF was administered at doses of 1.5 to 9 grams daily in two divided doses in cycles of 14 each with a 14 day gap.

Tumor size progression was monitored through CT scans and tumor markers where available. CT scans were performed at baseline and after each 8-week period once treatment was initiated, and also compared with a pre-baseline scan conducted prior to enrollment in the study. Tumor markers are measured every 4 weeks. Blood samples were collected to measure subclasses of circulating lymphocytes and NK cell activity. Plasma, serum and blood cell extract samples were collected to measure circulating IL-18, IL-1, IL-2, and IL-4, IL-5, IL-10, IL-12 and IFN-γ.

Out of nineteen evaluable patients (those with a baseline CT scan and at least one post-treatment scan), nine patients (47%) exhibited stable disease by the RECIST criteria at the time of the first post-treatment scan. Patients with a broad range of tumor types showed a benefit from lactoferrin administration.

Table 12 shows the tumor response of five individual patients with different tumor types. In all cases, the percent growth of the tumor size prior to treatment of rhLF (the relevant duration of time is shown in parentheses) and the growth of the tumor in the ensuing two time periods, as measured by CT, showed a diminution in their rate of tumor growth or an actual shrinkage.

TABLE 12

Tumor Response of Patients Receiving Oral rhLF for treatment of Metastatic Cancer

| Patient # | Cancer | Pretreatment % Growth (Weeks) | Post Treatment 1 % Growth (Weeks) | Post Treatment 2 % Growth (Weeks) |
|---|---|---|---|---|
| # 204 | Breast | 40% (8) | 0% (10) | 0% (6.5) |
| # 106 | Melanoma | 24% (19) | −18% (11) | Not yet done |
| # 104 | Gastric | 25% (5.5) | 10% (10) | −5% (7) |
| # 102 | Ovarian | 30% (21) | −5% (10.5) | −7% (8.5) |
| # 007 | Lung | 160% (5.5) | 13% (7.5) | 12% (8.5) |

Example 11

Combination Therapy with Oral hLF in Humans

Recombinant human lactoferrin is orally administered to human patients to inhibit tumor growth either alone or in combination with standard anti-cancer regimens.

Briefly, rhLF is administered using the optimum regimen and doses identified in Example 10 and the standard anti-cancer regimen(s) for the selected tumor type is used as part of the combination therapy. The route of administration and regimen of the additional anti-cancer therapy is as approved by the FDA for that indication or as described in a peer reviewed publication.

Tumor size progression is monitored through CT scans and tumor markers where available. CT scans are performed at baseline and after each 8-week period once treatment is initiated. Tumor markers are measured every 4 weeks once treatment is initiated. Blood samples are collected to measure subclasses of circulating lymphocytes and NK cell activity. Plasma, serum and blood cell extract samples are collected to measure circulating IL-18, IL-1, IL-2, IL-4, IL-5, IL-10, and IL-12 and IFN-$\gamma$.

Example 12

Immunostimulation Following Administration of Oral RhLF

Balb/c naïve mice were treated orally with rhLF or placebo once a day for 3 days. One day later (day 4), mice were sacrificed and spleens collected. NK cells were separated using a magnetic bead cell sorting assay (MACS anti-NK-DX5) and counted. Cells were then tested in vitro for NK-activity against YAC targets using a lactate dehydrogenase (LDH) release test.

Figure 4:
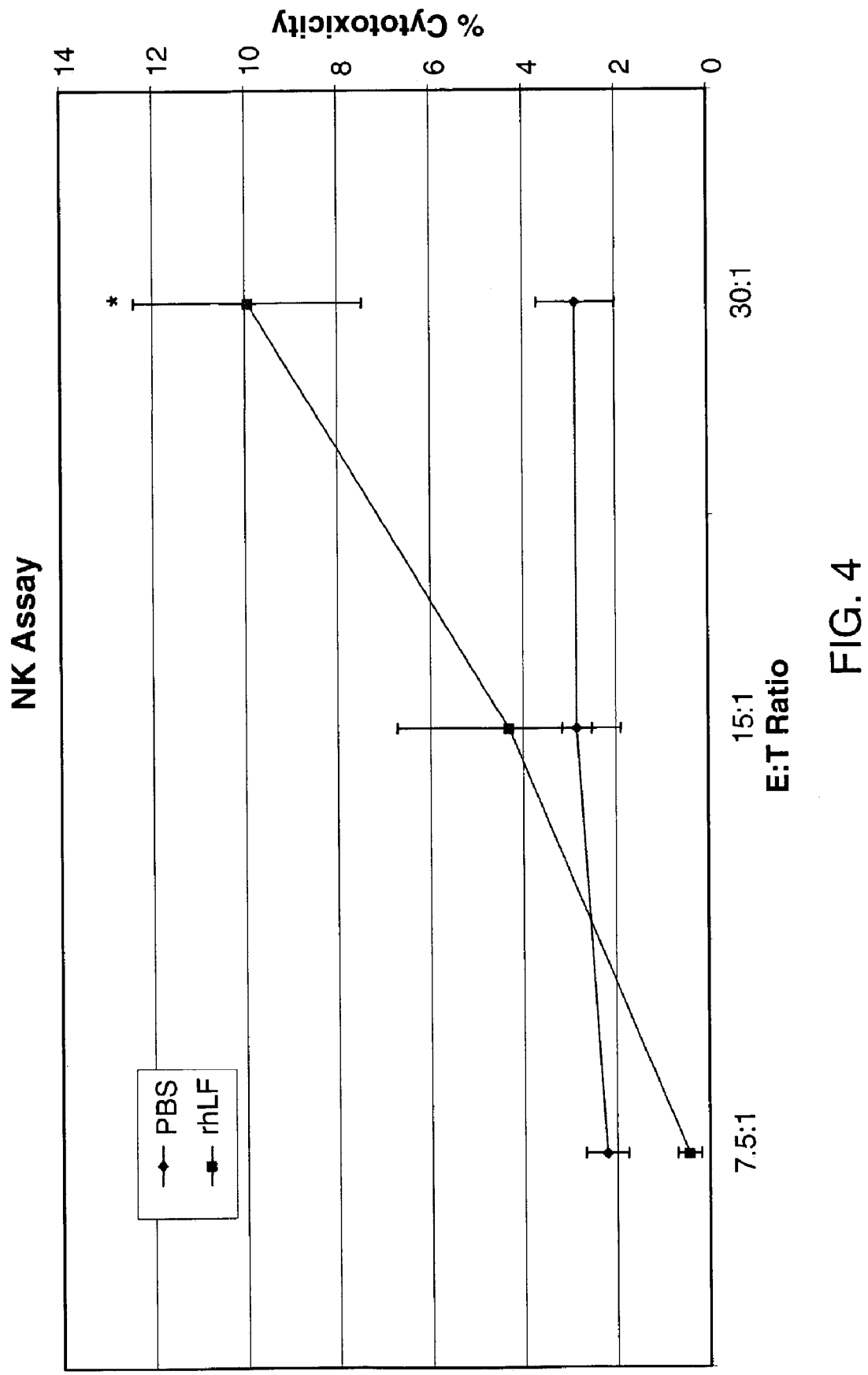
FIG. 4 shows the NK activity after treatment with lactoferrin.

As shown in FIG. 4, oral rhLF treatment resulted in a significant increase of NK activity ex-vivo against YAC-target cells. At a 30:1 E:T ratio rhLF administration resulted in a 243% relative increase over placebo-treated animals (from 2.86% to 9.81%; p<0.05).

Example 13

Effect of Intravenous Administration

Recombinant lactoferrin, bovine lactoferrin and native lactoferrin are intravenously administered to animals, preferably rats, and the production of IL-18, IL-1, IL-2, IL-4, IL-5, IL-10, IL-12 and IFN-gamma in the plasma, serum and blood packed cells are measured.

Briefly, rats are treated for fourteen consecutive days with 0.05 µg to 1000 µg per dose. For a control, rats are only administered the pharmaceutical carrier. At specific time points following administration of the LF or control for 0 days, 2 days, 3 days, 5 days, 9 days and 14 days, animals are weighed and blood and serum are collected. The levels of CD4+, CD8+ and NK cells are counted from the blood that was collected. Plasma, serum and an extract of the blood cells are used for cytokine ELISA assays.

Also, at 24 day time point, animals are sacrificed and tissues are removed for further analysis. Tissues are homogenized using a lysis buffer consisting of PBS, 1% Nonidet P-40, 0.5% sodium deoxycholate, and 0.1% sodium dodecyl sulphate containing 10 µg/ml PhenylMetheylsulfonyl fluoride. Homogenate is centrifuged at 15,000 rpm for 10 minutes and the supernatant stored at –80 C. till it is tested for the cytokines IL-18, IL-1, IL-2, IL-4, IL-5, IL-10, IL-12 and IFN-gamma.

Example 14

Combination Chemotherapy of Intravenously RhLF with Other Agents

Tumor cells to be tested are injected into the right flank of athymic nude mice. Animals are administered rhLF intravenously alone and in combination with other anti-cancer regimens as described in Example 13. Control animals are treated with only the vehicle; no rhLF is administered to the control animals. rhLF is administered using regimens identified as being optimal in the trials described in Example 13. Anti-cancer therapy is administered using standard or published regimens. Therapy starts approximately 11 days after inoculation with tumor cells to allow formation of established tumors or at such other time as is generally done with standard or published regimens.

The efficacy of individual and combination treatments are evaluated by measuring the solid tumor size during and at the end of the experiment; the body weights are also determined at the time of tumor measurements.

Example 15

Intravenous Administration of hLF in Humans

Recombinant lactoferrin is intravenously administered to patients to inhibit tumor growth.

Briefly, rhLF at a dose of 500 mg per day for eight days to patients suffering from unresectable or metastatic cancer. Alternatively, rhLF is administered for one to eight days to patients suffering from metastatic cancer in daily doses of 0.1, 1, 10, 100, and 1000 mg. The dose is administered intravenously.

Tumor size progression is monitored through CT scans and tumor markers where available. CT scans are performed at baseline and after each 8-week period once treatment is initiated. Tumor markers are measured every 4 weeks. Blood samples are collected to measure subclasses of circulating lymphocytes and NK cell activity. Plasma, serum and blood cell extract samples are collected to measure circulating IL-18, IL-1, IL-2, IL-4, IL-5, IL-10, IL-12 and IFN-$\gamma$.

Example 16

Combination Therapy with Intravenous hLF

Recombinant lactoferrin is intravenously administered to patients to inhibit tumor growth either alone or in combination with standard anti-cancer regimens.

Briefly, rhLF is administered using the optimum regimen and doses identified in Example 15 and the standard anti-cancer regimen(s) for the selected tumor type is used as part of the combination therapy. The route of administration and regimen of the additional anti-cancer therapy is as approved by the FDA for that indication or as described in a peer reviewed publication.

Tumor size progression is monitored through CT scans and tumor markers where available. CT scans are performed at baseline and after each 8-week period once treatment is initiated. Tumor markers are measured every 4 weeks once treatment is initiated. Blood samples are collected to measure subclasses of circulating lymphocytes and NK cell activity. Plasma, serum and blood cell extract samples are collected to measure circulating IL-18, IL-1, IL-2, IL-4, IL-5, IL-10, IL-12 and IFN-$\gamma$.

Example 17

Activity of Intratumoral RhLF

O12 human oropharyngeal squamous cell carcinoma tumor cells were injected to the right flank of athymic nude mice. Recombinant human lactoferrin and vehicle controls were dosed via intratumoral injection. Each animal was administered different concentrations of rhLF in 50 µL doses consisting of four separate injections of approximately 12.5 µL of the dose, at different directions and angles (approximately S/N/E/W) to ensure that the dose was distributed evenly throughout the tumor (fanning).

TABLE 13

Treatment schedule of intratumor injections of recombinant human lactoferrin in O12 human squamous carcinoma cell tumors in nude mice

| Group | Regimen | Dose of rhLF per animal in group | | | | | |
|---|---|---|---|---|---|---|---|
| | | 0 | 1 | 2 | 3 | 4 | 5 |
| E. A | Once on day 1, kill 8 days later (nude mice) | 0 | 100 µg | 250 µg | 500 µg | 250 µg* | na |
| C | Twice/day for 8 days starting on Day 11 after inoculation, kill on Day 20 (nude mice) | 0 | 25 µg | 50 µg | 125 µg | 250 µg | 500 µg |

Table 13 shows the regimen followed for each experimental group and the dose of rhLF per injection for each animal per group. In this study, rhLF was administered directly into the tumor. Each animal was tracked daily for tumor growth by external caliper measurements of the protruding tumor.

Using this model, significant reduction of tumor growth was evident in both rhLF treated groups relative to the control animals. Compared to the median tumor size for the pooled placebo samples from groups A and C, the rates of tumor growth in animals receiving a single dose of rhLF (Group A) were reduced by 50% on day 11 after the administration of rhLF ($p<0.05$). The rates of tumor growth in animals dosed twice daily (Group C) were reduced by 56% when compared to the pooled control group ($p<0.01$) (See FIG. 5).

Example 18

Immune Stimulation Following Intratumoral RhLF

Normal C3H/HeJ mice were implanted with one of two mouse tumors following the methodology described in Example 17. Tumors used were SCCVII and RIF mouse tumor cell lines. Following establishment of the tumors in the mice, tumors were injected intratumorally daily for 4 days with 250 or 500 µg rhLF per dose or with vehicle control. Twenty four hours following the last intratumoral injection, animals were sacrificed and the blood examined for lymphocyte populations. The number of circulating lymphocytes were increased by 34% to 56% relative to the placebo treated control animals (Table 14).

TABLE 14

Increase in circulating lymphocytes following intratumoral administration of rhLF

| Number of Cells | CD3+ | CD4+ | CD8+ |
|---|---|---|---|
| Placebo | 2104 | 1800 | 785 |
| rhLF treated | 3291 | 2621 | 1054 |
| Increase with rhLF | 56% | 46% | 34% |

Example 19

Combination Chemotherapy of hLF with Other Agents

Tumor cells to be tested are injected into the right flank of athymic nude mice. Animals are administered rhLF intratumorally alone and in combination with other anti-cancer regimens as described in Example 1 or Example 17. Control animals are treated with only the vehicle; no rhLF is administered to the control animals. Anti-cancer therapy is administered using standard or published regimens. Therapy starts approximately 11 days after inoculation with tumor cells to allow formation of established tumors or at such other time as is generally done with standard or published regimens.

The efficacy of individual and combination treatments are evaluated by measuring the solid tumor size during and at the end of the experiment; the body weights are also determined at the time of tumor measurements.

Example 20

Intratumoral Administration of hLF

Recombinant lactoferrin is intratumorally administered to patients to inhibit tumor growth.

Briefly, rhLF at a dose of 1000 µg per day for eight days to patients suffering from unresectable or metastatic cancer. Alternatively, rhLF is administered for one to eight days to patients suffering from metastatic cancer in daily doses of 10, 50, 100, 500 and 1000 µg. The dose is administered intratumorally.

Tumor size progression is monitored through CT scans and tumor markers where available. CT scans are performed at baseline and after each 8-week period once treatment is initiated. Tumor markers are measured every 4 weeks. Blood samples are collected to measure subclasses of circulating lymphocytes and NK cell activity. Plasma, serum and blood cell extract samples are collected to measure circulating IL-18, IL-1, IL-2, IL-4, IL-5, IL-10, IL-12 and IFN-γ.

Example 21

Combination Therapy with Intratumoral hLF

Recombinant lactoferrin is intratumorally administered to patients to inhibit tumor growth either alone or in combination with standard anti-cancer regimens.

Briefly, rhLF is administered using the optimum regimen and doses identified in Example 20 and the standard anti-cancer regimen(s) for the selected tumor type is used as part of the combination therapy. The route of administration and regimen of the additional anti-cancer therapy is as approved by the FDA for that indication or as described in a peer reviewed publication.

Tumor size progression is monitored through CT scans and tumor markers where available. CT scans are performed at baseline and after each 8-week period once treatment is initiated. Tumor markers are measured every 4 weeks once treatment is initiated. Blood samples are collected to measure subclasses of circulating lymphocytes and NK cell activity. Plasma, serum and blood cell extract samples are collected to measure circulating IL-18, IL-1, IL-2, IL-4, IL-5, IL-10, IL-12 and IFN-γ.

Example 22

Topical Administration of hLF in Humans

Recombinant lactoferrin in a gel formulation is administered to patients to inhibit tumor growth.

Briefly, rhLF gel at strengths of 1%, 2.5% or 8.5% is applied twice a day to a skin or subcutaneous cancerous lesion in a patient with metastatic disease. Application of rhLF gel continues till tumor progression.

Size progression of the metastatic disease is monitored through CT scans and tumor markers where available. CT scans are performed at baseline and after each 8-week period once treatment is initiated. Tumor markers are measured every 4 weeks. Blood samples are collected to measure subclasses of circulating lymphocytes and NK cell activity. Plasma, serum and blood cell extract samples are collected to measure circulating IL-18, IL-1, IL-2, IL-4, IL-5, IL-10, IL-12 and IFN-γ.

Example 23

Combination Therapy with Topical hLF

Recombinant lactoferrin in a gel formulation is administered to patients to inhibit tumor growth either alone or in combination with standard anti-cancer regimens.

Briefly, rhLF is administered using the optimum regimen and doses identified in Examples 22 and the standard anti-cancer regimen(s) for the selected tumor type is used as part of the combination therapy. The route of administration and regimen of the additional anti-cancer therapy is as approved by the FDA for that indication or as described in a peer reviewed publication.

Size progression of the metastatic disease is monitored through CT scans and tumor markers where available. CT scans are performed at baseline and after each 8-week period once treatment is initiated. Tumor markers are measured every 4 weeks once treatment is initiated. Blood samples are collected to measure subclasses of circulating lymphocytes and NK cell activity. Plasma, serum and blood cell extract samples are collected to measure circulating IL-18, IL-1, IL-2, IL-4, IL-5, IL-10, IL-12 and IFN-γ.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,629,001
Bezault J et. al., *Cancer Res.* 1994, 54(9):2310-2.
Broxmeyer H E. *Blood.* 1983; 61:982-993.
Damiens E, et al., *Biochim Biophys Acta.* 1998, 1402(3):277-87.
Dhennin-Duthille I, et al., *J Cell Biochem.* 2000, 79(4):583-93.
Erlandsson, *Cancer Genet. Cytogenet,* 104:1-18, 1998.
Gahr M, et al., *J Leukocyte Biol.* 1991; 49: 427-33.
Gertig and Hunter, *Semin. Cancer Biol.,* 8(4):285-298, 1997.
Horowitz D A, et al., *J Immunol.* 1984; 132: 2370-4.
Iigo M, et al., *Clin Exp Metastasis.* 1999, 17(1):35-40.\
Kolmel, *J. Neurooncol.,* 38:121-125, 1998.
Kuhara T, et al., *Nutr Cancer.* 2000, 38(2):192-9.
Magi-Galluzzi et al., *Anal. Quant. Cytol. Histol.,* 20:343-350, 1998.
Mangray and King, *Front Biosci.,* 3:D1148-1160, 1998.
Masuda C, et al. *Jpn J Cancer Res.* 2000, 91(6):582-8.
Mayer, *Radiat Oncol Investig.* 6:281-8, 1998.
Mumby and Walter, *Cell Regul.,* 2:589-598, 1991.
Natoli et al., *Biochem. Pharmacol.,* 56(8):915-920, 1998.
Ohara, *Acta Oncol.* 37:471-4, 1998.
Shau H, et al., *J Leukocyte Biol.* 1992; 51:343-9.
Solyanik et al., *Cell Prolif.,* 28:263-278, 1995.
Spik G, et al., *Adv Exp Med Biol.* 1994; 357:13-9.
Stokke et al., *Cell Prolif.,* 30(5):197-218, 1997.
Tanaka T, et al. *Jpn J Cancer Res.* 2000, 91(1):25-33.
Tsuda H, et al., *Biofactors.* 2000; 12(1-4):83-8.
Ushida Y, et al. *Jpn J Cancer Res.* 1999, 90(3):262-7.
Wang W P, et al., *Jpn J Cancer Res.* 2000, 91(10):1022-7.
Yoo Y C, et al., *Adv Exp Med Biol.* 1998, 443:285-91.
Yoo Y C, et al., *Jpn J Cancer Res.* 1997, 88(2):184-90.

Although the present invention and its advantages have been described in detail, it should be understood that various changes, substitutions and alterations can be made herein without departing from the spirit and scope of the invention as defined by the appended description. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended descriptions are intended to include within their scope such processes, machines, manufacture, compositions of matter, means, methods, or steps.

What is claimed is:

1. A method of treating an established solid Renal cell carcinoma comprising the step of administering orally to a human subject a mature native human lactoferrin protein as a monotherapy in an amount sufficient to reduce the rate of growth or shrink the established solid Renal cell carcinoma in the human subject.

2. A method of treating an established solid Non-small cell lung cancer a comprising the step of administering orally to a human subject a mature native human lactoferrin protein as a monotherapy in an amount sufficient to reduce the rate of growth or shrink the established solid Non-small cell lung cancer in the human subject.

* * * * *